US011013704B2

(12) United States Patent
Zhang et al.

(10) Patent No.: US 11,013,704 B2
(45) Date of Patent: May 25, 2021

(54) COMPOUNDS SUPPORTS HEMATOPOIETIC STEM CELLS AND RED BLOOD CELLS

(71) Applicant: The Board of Regents of the University of Texas System, Austin, TX (US)

(72) Inventors: Chengcheng Zhang, Dallas, TX (US); Yi Liu, Dallas, TX (US); Junke Zheng, Shanghai (CN); Mi Deng, Plano, TX (US); Chuo Chen, Dallas, TX (US); Jiawei Liu, Changsha (CN)

(73) Assignee: The Board of Regents of the University of Texas System, Austin, TX (US)

( * ) Notice: Subject to any disclaimer, the term of this patent is extended or adjusted under 35 U.S.C. 154(b) by 961 days.

(21) Appl. No.: 15/312,790

(22) PCT Filed: May 12, 2015

(86) PCT No.: PCT/US2015/030352
§ 371 (c)(1),
(2) Date: Sep. 20, 2017

(87) PCT Pub. No.: WO2015/183545
PCT Pub. Date: Dec. 3, 2015

(65) Prior Publication Data
US 2017/0304240 A1    Oct. 26, 2017

Related U.S. Application Data

(60) Provisional application No. 62/003,969, filed on May 28, 2014.

(51) Int. Cl.
| | | |
|---|---|---|
| *A61K 31/194* | (2006.01) | |
| *A61K 31/197* | (2006.01) | |
| *C12N 5/078* | (2010.01) | |
| *C12N 5/0789* | (2010.01) | |
| *A61K 31/155* | (2006.01) | |
| *A61K 31/20* | (2006.01) | |
| *C07C 279/14* | (2006.01) | |
| *A61K 45/06* | (2006.01) | |
| *A61K 35/65* | (2015.01) | |
| *A61K 38/01* | (2006.01) | |

(52) U.S. Cl.
CPC .......... *A61K 31/194* (2013.01); *A61K 31/155* (2013.01); *A61K 31/197* (2013.01); *A61K 31/20* (2013.01); *A61K 45/06* (2013.01); *C12N 5/0634* (2013.01); *C12N 5/0647* (2013.01); *A61K 35/65* (2013.01); *A61K 38/012* (2013.01); *C07C 279/14* (2013.01)

(58) Field of Classification Search
CPC .. A61K 31/155; A61K 31/194; A61K 31/197; A61K 31/20; A61K 45/06; A61K 35/65; C07C 279/14; C12N 5/0634; C12N 5/0647
See application file for complete search history.

(56) References Cited

U.S. PATENT DOCUMENTS

| | | |
|---|---|---|
| 2006/0040334 A1 | 2/2006 | Thompson |
| 2011/0206781 A1 | 8/2011 | Zon et al. |
| 2013/0090488 A1 | 4/2013 | Dietz |

FOREIGN PATENT DOCUMENTS

| | | | |
|---|---|---|---|
| CN | 1 413 618 | 4/2003 | |
| CN | 101 628 091 | 1/2010 | |
| JP | S62 207214 | 9/1987 | |
| WO | WO-2009025957 A1 * | 2/2009 | ......... C07K 14/4705 |
| WO | WO 2006/024174 | 3/2016 | |

OTHER PUBLICATIONS

Google English Translation of CN1413618, accessed on Jan. 16, 2020.*
Google English Translation of CN100534493, accessed on Jan. 16, 2020.*
Barry et al., "GC/MS comparison of the West Indian aphrodisiac "Love Stone" to the Chinese medication "char su": bufotenine and related bufadienolides," *J. Forensic Sci.*, 41:1068-1073, 1996.
Chemical Abstract Database for Ito, "Water-soluble fraction of sen-so (toad cake)," Database Accesion No. 1963:468480, Date Accessed: Nov. 28, 2017.
Extended European Search Report issued in corresponding European Application No. 15798851.1, dated Dec. 8, 2017.
Gao et al., "Comparison of toad venoms from different Bufo species by HPLC and LC-DAD-MS/MS," *J. Ethnopharmacol.*, 131(2):368-376, 2010.
International Preliminary Report on Patentability issued in corresponding PCT Application No. PCT/US2015/030352, dated Dec. 8, 2016.
International Search Report and Written Opinion issued in corresponding PCT Application No. PCT/US2015/030352, dated Aug. 13, 2015.

(Continued)

*Primary Examiner* — James H Alstrum-Acevedo
*Assistant Examiner* — Erinne R Dabkowski
(74) *Attorney, Agent, or Firm* — Parker Highlander PLLC

(57) ABSTRACT

The present disclosure relates to methods of using a compound to induce regeneration of hematopoietic stem cells or increase the recovery of red blood cells. In some aspects, the present methods can be used to with or in place of erythropoietin in patients to mitigate the side effects of erythropoietin.

10 Claims, 10 Drawing Sheets

(56) References Cited

OTHER PUBLICATIONS

Jing et al., "Rapid identification of primary constituents in paranoid gland secretions of the Australian cane toad using HPLC/MS-Q-TOF: Australian cane toad paratoid gland chemistry," *Biomed. Chromatogr.*, 27(6):685-687, 2013.
Qi et al., "Apoptosis-inducing effect of cinobufacini, Bufo bufo gargarizans Cantor skin extract, on human hepatoma cell line BEL-7402," *Drug Discov. Ther.*, 2(6):339-343, 2008.
Schmeda-Hirchmann et al., "Antiproliferative activity and new argininyl bufadienolide esters from the "cururú" toad *Rhinella (Bufo) schneideri*," *J. Ethnopharmacol.*, 155, 1076-1085, 2014.
Xu et al., "Simultaneous determination of five main active bufadienolides of Chan Su in rat plasma by liquid chromatography tandem mass spectrometry," *J. Chromatogr. B Analyt. Technol. Biomed. Life Sci.*, 859:157-163, 2007.
Ye and Guo, "Analysis of bufadienolides in the Chinese drug ChanSu by high-performance liquid chromatography with atmospheric pressure chemical ionization tandem mass spectrometry," *Rapid Commun. Mass Spectrom*, 19:1881-1892, 2005.

\* cited by examiner

*Suberoylarginine*

COMPOUNDS SUPPORTS HEMATOPOIETIC STEM CELLS AND RED BLOOD CELLS

This application is a national phase application under 35 U.S.C. § 371 of International Application No. PCT/US2015/030352, filed May 12, 2015, which claims benefit of priority to U.S. Provisional Application Ser. No. 62/003,969, filed May 28, 2014, the entire contents of each of which are hereby incorporated by reference.

BACKGROUND

1. Field

The present disclosure generally relates to the fields of hematology and compounds for the modulating the activity of hematopoietic stem cells and production of red blood cells. More specifically, it relates to the use of compounds to regenerate hematopoietic stem cells and increase the recovery of red blood cells.

2. Description of Related Art

Currently, over $10 billion are spent annually on erythropoietin (EPO) which is the only red blood cell-stimulating drug on the market. Furthermore, erythropoietin has significant side effects such as hypertension and other cardiovascular complications that limit its effectiveness and the percentage of patients for which it can be used.

Traditional Chinese medicine provides a rich resource of potential drugs. Chan Su (Venenum *Bufonis*), the dry secretion from the skin glands of *Bufo gargarizans Cantor* or *B. melanostictus Schneider*, has been used for hundreds of years in traditional Chinese medicine. In the last half century, extracts from Chan Su have been shown to have cardiotonic and anti-cancer properties. Chan Su is composed of more than 40 compounds, including indole alkaloids (serotonin, bufotenine, bufatenidine, and cinobufotenine) and steroidal cardiac glycosides, many of which are toxic and anti-proliferative.

Liu et al. reported that a specially prepared form of Chan Su extract, in which the toxic lipid-soluble components are removed, is effective in treatment of certain anemia patients. In the published study, 88% of treated anemia patients showed significant improvement, whereas only 6.6% of the patients treated with the control drug did. An increase in reticulocytes was observed 3-7 days after the treatment, followed by increased in levels of other hematopoietic lineages. Importantly, the Chan Su extract did not show any apparent toxicity in patients after treatment for up to two years. Furthermore, the injection of this form of Chan Su into sublethally irradiated mice significantly enhanced the recovery of erythroid, myeloid, and some lymphoid progenitors and differentiated cells (Liu et al., 1986). These results suggest that Chan Su stimulates the regeneration of hematopoietic system in vivo.

With an estimated 26 million Americans suffering from chronic kidney disease which can lead to chronic anemia, the need for new compounds that can be used to promote red blood cell proliferation and thus treat anemia and other bone marrow failure diseases is growing.

SUMMARY

The present disclosure provides a method of treating a deficiency in red blood cells comprising administering to a patient a pharmaceutically effectively amount of a compound wherein the compound is chemically synthesized or is provided in a substantially isolated or purified form from a natural source and is of the formula:

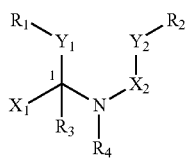

(I)

wherein: $R_1$ and $R_2$ are each independently selected from amino, hydroxy, carboxy, guanidinyl, alkylguanidinyl$_{(C\leq18)}$, substituted alkylguanidinyl$_{(C\leq18)}$, urea, alkylurea$_{(C\leq18)}$, substituted alkylurea$_{(C\leq18)}$, boronic acid, boronic ester$_{(C\leq18)}$, substituted boronic ester$_{(C\leq18)}$, phosphate, sulfonyl, sulfinyl, mercapto, cyano, acyl$_{(C\leq12)}$, substituted acyl$_{(C\leq12)}$, amido$_{(C\leq12)}$, substituted amido$_{(C\leq12)}$, alkoxy$_{(C\leq12)}$, substituted alkoxy$_{(C\leq12)}$, alkylamino$_{(C\leq12)}$, substituted alkylamino$_{(C\leq12)}$, dialkylamino$_{(C\leq12)}$, substituted dialkylamino$_{(C\leq12)}$, alkylsulfonyl$_{(C\leq12)}$, substituted alkylsulfonyl$_{(C\leq12)}$, alkylphosphate$_{(C\leq12)}$, substituted alkylphosphate$_{(C\leq12)}$, dialkylphosphate$_{(C\leq12)}$, substituted dialkylphosphate$_{(C\leq12)}$, or —C(O)R$_5$ wherein R$_5$ is alkoxy$_{(C\leq12)}$ or substituted alkoxy$_{(C\leq12)}$; R$_3$ and R$_4$ are each independently selected from hydrogen, alkyl$_{(C\leq12)}$, or substituted alkyl$_{(C\leq12)}$; or R$_3$ is taken together with Y$_2$ to form a cyclic structure comprising 5, 6, 7, 8, 9, 10, 11, or 12 atoms; X$_1$ is amino, carboxy, cyano, guanidinyl, hydroxy, mercapto, phosphate, phosphoamino, sulfinyl, sulfonyl, urea, —C(O)R$_6$, —C(NH)R$_6$, or —S(O)$_2$R$_6$ wherein R$_6$ is hydroxy; amino; alkoxy$_{(C\leq12)}$; alkylamino$_{(C\leq12)}$; dialkylamino$_{(C\leq12)}$; or a substituted version of any of the last three groups, amido$_{(C\leq12)}$, alkylsulfonyl$_{(C\leq12)}$, alkylphosphate$_{(C\leq12)}$, dialkylphosphate$_{(C\leq12)}$, alkylphosphoamino$_{(C\leq12)}$, dialkylphosphoamino$_{(C\leq12)}$ or a substituted version of any of the last six groups; X$_2$ is —C(O)—, —C(NR')—, —NR'C(O)NR"—, —NR'C(S)NR"—, —NR'C(NR")NR'"—, —S(O)$_2$—, —S(O)$_2$NR'—, —NR'S(O)$_2$—, —P(O)(OR')—, —P(O)(NR'R")—, —(NR'R")P(O)—, —P(O)(OR')—, —P(O)(NR'R")—, —(NR'R")P(O)—, —OP(O)(OR')—, —P(O)(OR')O—, —P(O)(NR'R")O—, —OP(O)(NR'R")—, —NR'"(NR'R")P(O)—, —(NR'R")P(O)NR'"—, wherein R', R", and R'" are each independently hydrogen, alkyl$_{(C\leq8)}$, or substituted alkyl$_{(C\leq8)}$; Y$_1$ and Y$_2$ are each independently a covalent bond, alkanediyl$_{(C\leq12)}$, alkenediyl$_{(C\leq12)}$, alkynediyl$_{(C\leq12)}$, arenediyl$_{(C\leq12)}$, alkoxydiyl$_{(C\leq12)}$, alkylaminodiyl$_{(C\leq12)}$, or a substituted version of any of these groups; or when Y$_2$ is taken together with R$_3$ to form a cyclic structure comprising 5, 6, 7, 8, 9, 10, 11, or 12 atoms and Y$_2$ is alkanetriyl$_{(C\leq12)}$, alkenetriyl$_{(C\leq12)}$, alkynetriyl$_{(C\leq12)}$, arenetriyl$_{(C\leq12)}$, alkoxytriyl$_{(C\leq12)}$, alkylaminotriyl$_{(C\leq12)}$, or a substituted version of any of these groups; and carbon 1 is in the R configuration, S configuration, or a mixture thereof; or a pharmaceutically acceptable salt or optical isomer thereof. In some embodiments, the compound is further defined as:

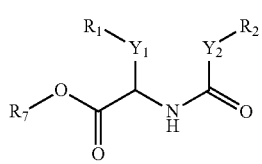

(II)

wherein: $R_1$ and $R_2$ are each independently selected from amino, hydroxy, carboxy, guanidinyl, alkylguanidinyl$_{(C≤18)}$, substituted alkylguanidinyl$_{(C≤18)}$, urea, alkylurea$_{(C≤18)}$, substituted alkylurea$_{(C≤18)}$, boronic acid, boronic ester$_{(C≤18)}$, substituted boronic ester$_{(C≤18)}$, phosphate, sulfonyl, sulfinyl, mercapto, cyano, acyl$_{(C≤12)}$, substituted acyl$_{(C≤12)}$, amido$_{(C≤12)}$, substituted amido$_{(C≤12)}$, alkoxy$_{(C≤12)}$, substituted alkoxy$_{(C≤12)}$, alkylamino$_{(C≤12)}$, substituted alkylamino$_{(C≤12)}$, dialkylamino$_{(C≤12)}$, substituted dialkylamino$_{(C≤12)}$, alkylsulfonyl$_{(C≤12)}$, substituted alkylsulfonyl$_{(C≤12)}$, alkylphosphate$_{(C≤12)}$, substituted alkylphosphate$_{(C≤12)}$, dialkylphosphate$_{(C≤12)}$, substituted dialkylphosphate$_{(C≤12)}$, or —C(O)$R_5$ wherein $R_5$ is alkoxy$_{(C≤12)}$ or substituted alkoxy$_{(C≤12)}$; $R_7$ is hydrogen, alkyl$_{(C≤12)}$, or substituted alkyl$_{(C≤12)}$; and $Y_1$ and $Y_2$ are each independently a covalent bond, alkanediyl$_{(C≤12)}$, alkenediyl$_{(C≤12)}$, alkynediyl$_{(C≤12)}$, arenediyl$_{(C≤12)}$, alkoxydiyl$_{(C≤12)}$, alkylaminodiyl$_{(C≤12)}$, or a substituted version of any of these groups; or a pharmaceutically acceptable salt or optical isomer thereof. In some embodiments, compound is further defined as:

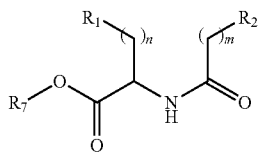

(III)

wherein: $R_1$ and $R_2$ are each independently selected from amino, hydroxy, carboxy, guanidinyl, alkylguanidinyl$_{(C≤18)}$, substituted alkylguanidinyl$_{(C≤18)}$, urea, alkylurea$_{(C≤18)}$, substituted alkylurea$_{(C≤18)}$, boronic acid, boronic ester$_{(C≤18)}$, substituted boronic ester$_{(C≤18)}$, phosphate, sulfonyl, sulfinyl, mercapto, cyano, acyl$_{(C≤12)}$, substituted acyl$_{(C≤12)}$, amido$_{(C≤12)}$, substituted amido$_{(C≤12)}$, alkoxy$_{(C≤12)}$, substituted alkoxy$_{(C≤12)}$, alkylamino$_{(C≤12)}$, substituted alkylamino$_{(C≤12)}$, dialkylamino$_{(C≤12)}$, substituted dialkylamino$_{(C≤12)}$, alkylsulfonyl$_{(C≤12)}$, substituted alkylsulfonyl$_{(C≤12)}$, alkylphosphate$_{(C≤12)}$, substituted alkylphosphate$_{(C≤12)}$, dialkylphosphate$_{(C≤12)}$, substituted dialkylphosphate$_{(C≤12)}$, or —C(O)$R_5$ wherein $R_5$ is alkoxy$_{(C≤12)}$ or substituted alkoxy$_{(C≤12)}$; $R_7$ is hydrogen, alkyl$_{(C≤12)}$, or substituted alkyl$_{(C≤12)}$; and m and n are each independently selected 0, 1, 2, 3, 4, 5, 6, 7, 8, 9, or 10; or a pharmaceutically acceptable salt or optical isomer thereof. In some embodiments, the compound is further defined by the formula:

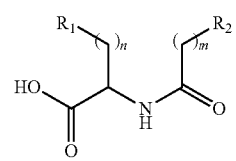

(IV)

wherein: $R_1$ and $R_2$ are each independently selected from amino, hydroxy, carboxy, guanidinyl, alkylguanidinyl$_{(C≤18)}$, substituted alkylguanidinyl$_{(C≤18)}$, urea, alkylurea$_{(C≤18)}$, substituted alkylurea$_{(C≤18)}$, boronic acid, boronic ester$_{(C≤18)}$, substituted boronic ester$_{(C≤18)}$, phosphate, sulfonyl, sulfinyl, mercapto, cyano, acyl$_{(C≤12)}$, substituted acyl$_{(C≤12)}$, amido$_{(C≤12)}$, substituted amido$_{(C≤12)}$, alkoxy$_{(C≤12)}$, substituted alkoxy$_{(C≤12)}$, alkylamino$_{(C≤12)}$, substituted alkylamino$_{(C≤12)}$, dialkylamino$_{(C≤12)}$, substituted dialkylamino$_{(C≤12)}$, alkylsulfonyl$_{(C≤12)}$, substituted alkylsulfonyl$_{(C≤12)}$, alkylphosphate$_{(C≤12)}$, substituted alkylphosphate$_{(C≤12)}$, dialkylphosphate$_{(C≤12)}$, substituted dialkylphosphate$_{(C≤12)}$, or —C(O)$R_5$ wherein $R_5$ is alkoxy$_{(C≤12)}$ or substituted alkoxy$_{(C≤12)}$; and m and n are each independently selected 1, 2, 3, 4, 5, 6, 7, 8, 9, or 10; or a pharmaceutically acceptable salt or optical isomer thereof. In some embodiments, the compound is further defined by the formula:

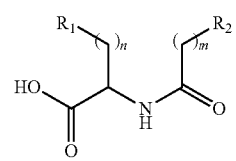

(IV)

wherein: $R_1$ and $R_2$ are each independently selected from amino, hydroxy, carboxy, guanidinyl, alkylguanidinyl$_{(C≤18)}$, substituted alkylguanidinyl$_{(C≤18)}$, urea, alkylurea$_{(C≤18)}$, substituted alkylurea$_{(C≤18)}$, alkylamino$_{(C≤12)}$, substituted alkylamino$_{(C≤12)}$, dialkylamino$_{(C≤12)}$, substituted dialkylamino$_{(C≤12)}$, or —C(O)$R_5$ wherein $R_5$ is alkoxy$_{(C≤12)}$ or substituted alkoxy$_{(C≤12)}$; and m and n are each independently selected 1, 2, 3, 4, 5, 6, 7, or 8; or a pharmaceutically acceptable salt or optical isomer thereof. In some embodiments, $R_1$ is amino. In other embodiments, $R_1$ is guanidinyl. In other embodiments, $R_1$ is urea. In some embodiments, $R_2$ is carboxy. In other embodiments, $R_2$ is amino. In some embodiments, $R_3$ is hydrogen. In some embodiments, $R_4$ is hydrogen. In some embodiments, $X_1$ is —C(O)$R_6$. In some embodiments, $R_6$ is alkoxy$_{(C≤12)}$ or substituted alkoxy$_{(C≤12)}$. In some embodiments, $R_6$ is —OCH$_3$. In some embodiments, $X_2$ is —C(O)—. In some embodiments, carbon 1 is in the R configuration. In other embodiments, carbon 1 is in the S configuration. In other embodiments, carbon 1 comprises a mixture of formulas in the R and S configuration. In some embodiments, m is 2, 3, 4, 5, 6, 7, or 8. In some embodiments, m is 2. In other embodiments, m is 4. In other embodiments, m is 5. In other embodiments, m is 6. In other embodiments, m is 7. In other embodiments, m is 8. In some embodiments, n is 2, 3, 4, 5, or 6. In some embodiments, n is 3. In other embodiments, n is 4. In some embodiments, $R_7$ is hydrogen. In some embodiments, the natural source is a toad skin extract. In some embodiments, the formula is not:

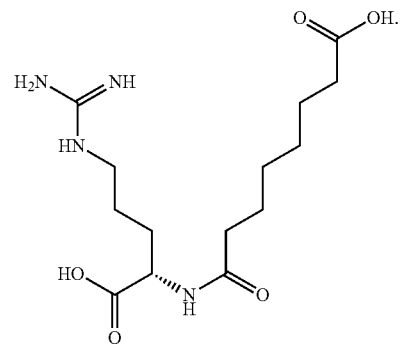 [SMILES: N=C(N)NCCC[C@H](NC(=O)CCCCCCC(=O)O)C(=O)O]

In some embodiments, $R_1$ is not guanidinyl, $R_2$ is not carboxyl, $R_3$ is not hydrogen, n is not 3 and m is not 6. In some embodiments, the compound is selected from the group consisting of:

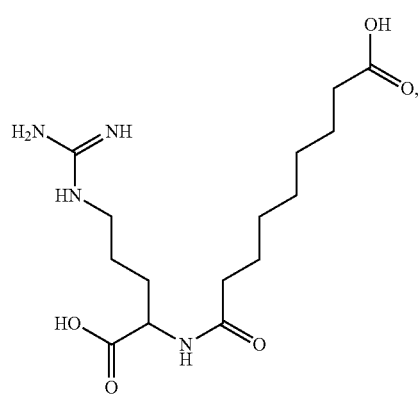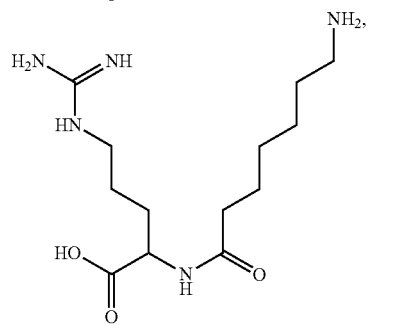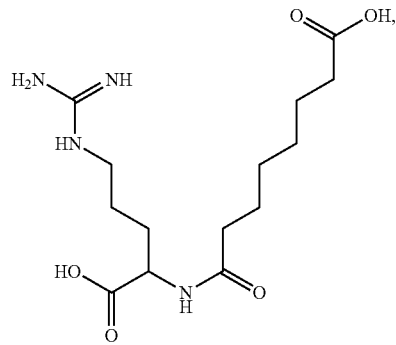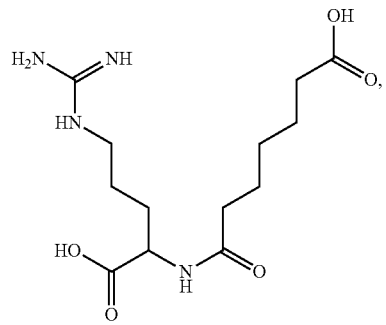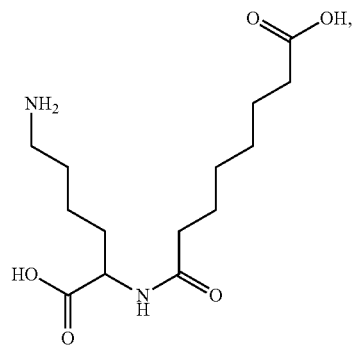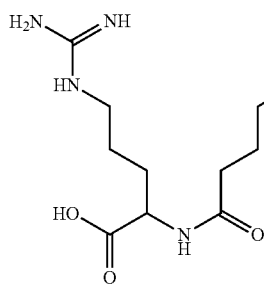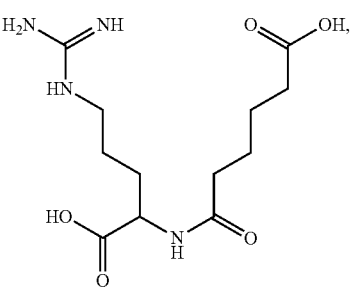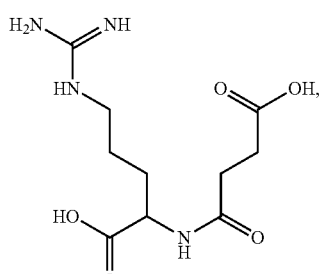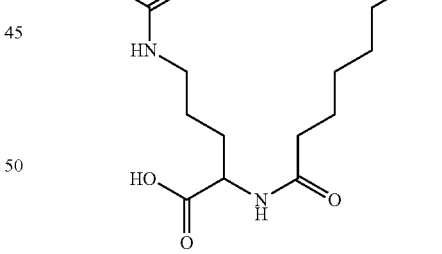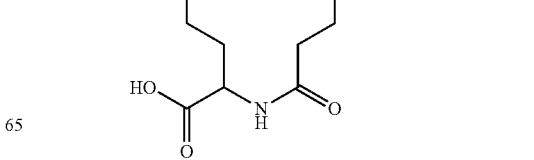

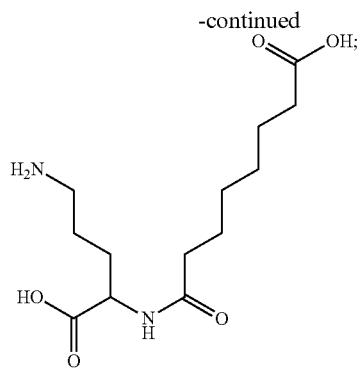
or a pharmaceutically acceptable salt or optical isomer thereof. In some embodiments, the compound is selected from the group consisting of:
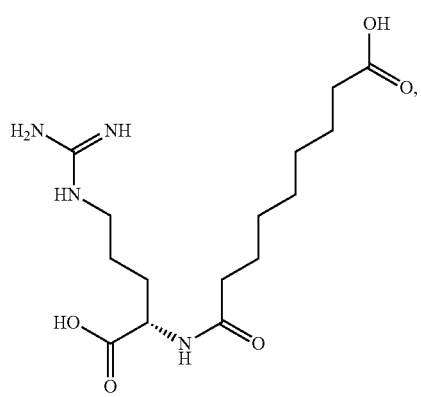
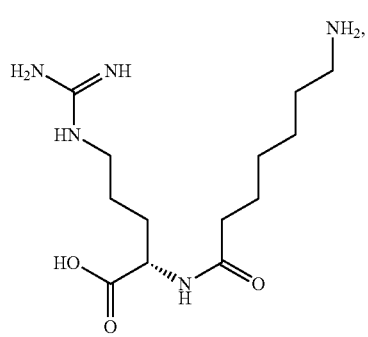
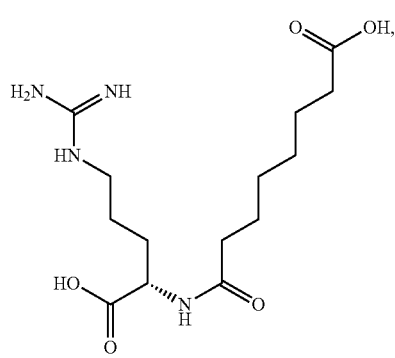
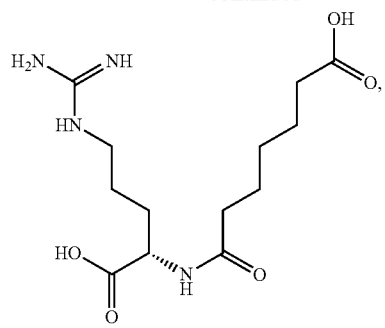
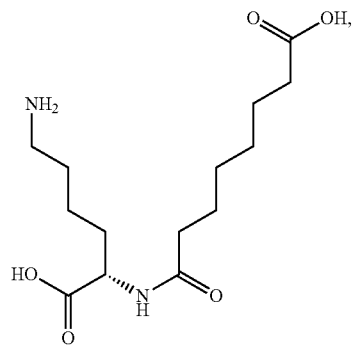
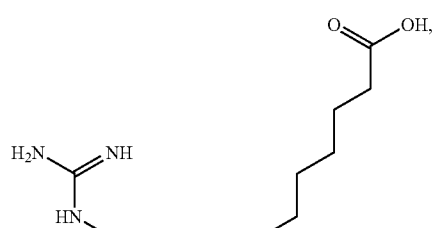
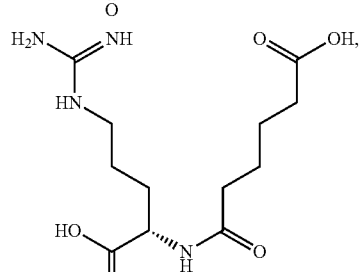
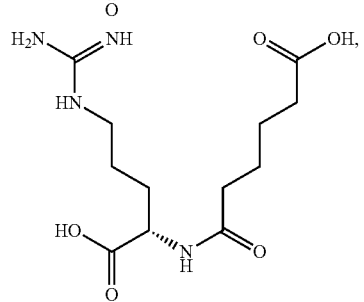
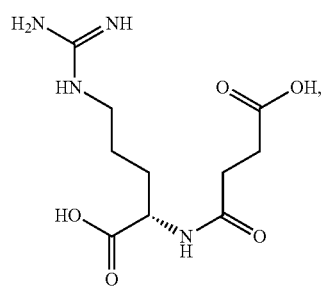

-continued

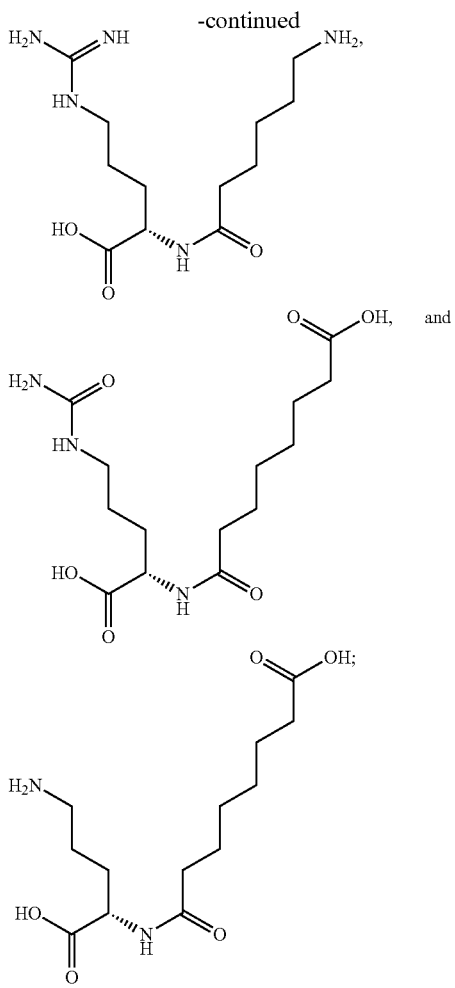

or a pharmaceutically acceptable salt thereof. In some embodiments, the compound is further defined as:

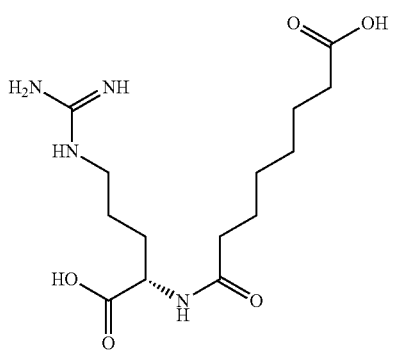 [SMILES: N=C(N)NCCC[C@H](NC(=O)CCCCCCC(=O)O)C(=O)O]

or a pharmaceutically acceptable salt thereof. In some embodiments, the deficiency in red blood cell is an anemia related to impaired production of red blood cells. In some embodiments, the anemia is aplastic anemia. In some embodiments, the anemia is a result of chronic kidney disease, chemotherapy, radiotherapy, hematopoietic stem cell transplantation, cancer, HIV or AIDS, rheumatoid arthritis, Crohn's disease or other chronic inflammatory disease, or bone marrow failure. In some embodiments, the compound is administered in combination with a second drug. In some embodiments, the second drug is erythropoietin. In some embodiments, the compound results in increased recovery of red blood cells. In some embodiments, the substantially isolated or purified form comprises the compound separated away from the other components of the toad skin extract. In some embodiments, the compound comprises 80% of the total mass of the substantially isolated or purified form. In some embodiments, the compound comprises 90% of the total mass of the substantially isolated or purified form. In other embodiments, the compound is in a chemical synthesized form.

In another aspect, the present disclosure provides a method of increasing the number of red blood cells in a patient suffering from erythropoietin toxicity comprising administering to the patient a pharmaceutically effective amount of the compound wherein the compound is chemically synthesized or is provided in a substantially isolated or purified form from a natural source and is of the formula:

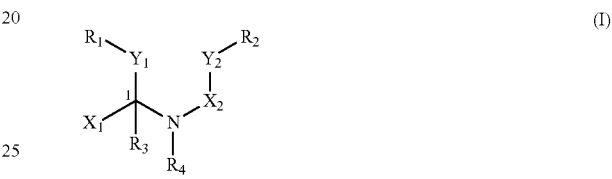

(I)

wherein: $R_1$ and $R_2$ are each independently selected from amino, hydroxy, carboxy, guanidinyl, alkylguanidinyl$_{(C \leq 18)}$, substituted alkylguanidinyl$_{(C \leq 18)}$, urea, alkylurea$_{(C \leq 18)}$, substituted alkylurea$_{(C \leq 18)}$, boronic acid, boronic ester$_{(C \leq 18)}$, substituted boronic ester$_{(C \leq 18)}$, phosphate, sulfonyl, sulfinyl, mercapto, cyano, acyl$_{(C \leq 12)}$, substituted acyl$_{(C \leq 12)}$, amido$_{(C \leq 12)}$, substituted amido$_{(C \leq 12)}$, alkoxy$_{(C \leq 12)}$, substituted alkoxy$_{(C \leq 12)}$, alkylamino$_{(C \leq 12)}$, substituted alkylamino$_{(C \leq 12)}$, dialkylamino$_{(C \leq 12)}$, substituted dialkylamino$_{(C \leq 12)}$, alkylsulfonyl$_{(C \leq 12)}$, substituted alkylsulfonyl$_{(C \leq 12)}$, alkylphosphate$_{(C \leq 12)}$, substituted alkylphosphate$_{(C \leq 12)}$, dialkylphosphate$_{(C \leq 12)}$, substituted dialkylphosphate$_{(C \leq 12)}$, or —C(O)R$_5$ wherein R$_5$ is alkoxy$_{(C \leq 12)}$ or substituted alkoxy$_{(C \leq 12)}$; $R_3$ and $R_4$ are each independently selected from hydrogen, alkyl$_{(C \leq 12)}$, or substituted alkyl$_{(C \leq 12)}$; or $R_3$ is taken together with $Y_2$ to form a cyclic structure comprising 5, 6, 7, 8, 9, 10, 11, or 12 atoms; $X_1$ is amino, carboxy, cyano, guanidinyl, hydroxy, mercapto, phosphate, phosphoamino, sulfinyl, sulfonyl, urea, —C(O)R$_6$, —C(NH)R$_6$, or —S(O)$_2$R$_6$ wherein R$_6$ is hydroxy; amino; alkoxy$_{(C \leq 12)}$; alkylamino$_{(C \leq 12)}$; dialkylamino$_{(C \leq 12)}$; or a substituted version of any of the last three groups, amido$_{(C \leq 12)}$, alkylsulfonyl$_{(C \leq 12)}$, alkylphosphate$_{(C \leq 12)}$, dialkylphosphate$_{(C \leq 12)}$, alkylphosphoamino$_{(C \leq 12)}$, dialkylphosphoamino$_{(C \leq 12)}$ or a substituted version of any of the last six groups; $X_2$ is —C(O)—, —C(NR')—, —NR'C(O)NR'''—, —NR'C(S)NR'''—, —NR'C(NR'')NR'''—, —S(O)$_2$—, —S(O)$_2$NR'—, —NR'S(O)$_2$—, —P(O)(OR')—, —P(O)(NR'R'')—, —(NR'R'')P(O)—, —P(O)(OR')—, —P(O)(NR'R'')—, —(NR'R'')P(O)—, —OP(O)(OR')—, —P(O)(OR')O—, —P(O)(NR'R'')O—, —OP(O)(NR'R'')—, —NR'''(NR'R'')P(O)—, —(NR'R'')P(O)NR'''—, wherein R', R'', and R''' are each independently hydrogen, alkyl$_{(C \leq 8)}$, or substituted alkyl$_{(C \leq 8)}$; $Y_1$ and $Y_2$ are each independently a covalent bond, alkanediyl$_{(C \leq 12)}$, alkenediyl$_{(C \leq 12)}$, alkynediyl$_{(C \leq 12)}$, arenediyl$_{(C \leq 12)}$, alkoxydiyl$_{(C \leq 12)}$, alkylaminodiyl$_{(C \leq 12)}$, or a substituted version of any of these groups; or when $Y_2$ is taken together with $R_3$ to form a cyclic structure comprising 5, 6, 7, 8, 9, 10, 11, or 12 atoms and $Y_2$ is alkanetriyl$_{(C \leq 12)}$, alkenetriyl$_{(C≤12)}$, alkynetriyl$_{(C≤12)}$, arenetriyl$_{(C≤12)}$, alkoxytriyl$_{(C≤12)}$, alkylaminotriyl$_{(C≤12)}$, or a substituted version of any of these groups; and carbon 1 is in the R configuration, S configuration, or a mixture thereof; or a pharmaceutically acceptable salt or optical isomer thereof. In some embodiments, the compound is further defined as:

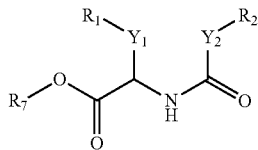
(II)

wherein: $R_1$ and $R_2$ are each independently selected from amino, hydroxy, carboxy, guanidinyl, alkylguanidinyl$_{(C≤18)}$, substituted alkylguanidinyl$_{(C≤18)}$, urea, alkylurea$_{(C≤18)}$, substituted alkylurea$_{(C≤18)}$, boronic acid, boronic ester$_{(C≤18)}$, substituted boronic ester$_{(C≤18)}$, phosphate, sulfonyl, sulfinyl, mercapto, cyano, acyl$_{(C≤12)}$, substituted acyl$_{(C≤12)}$, amido$_{(C≤12)}$, substituted amido$_{(C≤12)}$, alkoxy$_{(C≤12)}$, substituted alkoxy$_{(C≤12)}$, alkylamino$_{(C≤12)}$, substituted alkylamino$_{(C≤12)}$, dialkylamino$_{(C≤12)}$, substituted dialkylamino$_{(C≤12)}$, alkylsulfonyl$_{(C≤12)}$, substituted alkylsulfonyl$_{(C≤12)}$, alkylphosphate$_{(C≤12)}$, substituted alkylphosphate$_{(C≤12)}$, dialkylphosphate$_{(C≤12)}$, substituted dialkylphosphate$_{(C≤12)}$, or —C(O)$R_5$ wherein $R_5$ is alkoxy$_{(C≤12)}$ or substituted alkoxy$_{(C≤12)}$; $R_7$ is hydrogen, alkyl$_{(C≤12)}$, or substituted alkyl$_{(C≤12)}$; and $Y_1$ and $Y_2$ are each independently a covalent bond, alkanediyl$_{(C≤12)}$, alkenediyl$_{(C≤12)}$, alkynediyl$_{(C≤12)}$, arenediyl$_{(C≤12)}$, alkoxydiyl$_{(C≤12)}$, alkylaminodiyl$_{(C≤12)}$, or a substituted version of any of these groups; or a pharmaceutically acceptable salt or optical isomer thereof. In some embodiments, compound is further defined as:

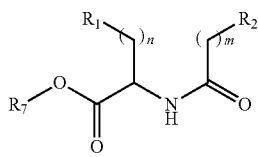
(III)

wherein: $R_1$ and $R_2$ are each independently selected from amino, hydroxy, carboxy, guanidinyl, alkylguanidinyl$_{(C≤18)}$, substituted alkylguanidinyl$_{(C≤18)}$, urea, alkylurea$_{(C≤18)}$, substituted alkylurea$_{(C≤18)}$, boronic acid, boronic ester$_{(C≤18)}$, substituted boronic ester$_{(C≤18)}$, phosphate, sulfonyl, sulfinyl, mercapto, cyano, acyl$_{(C≤12)}$, substituted acyl$_{(C≤12)}$, amido$_{(C≤12)}$, substituted amido$_{(C≤12)}$, alkoxy$_{(C≤12)}$, substituted alkoxy$_{(C≤12)}$, alkylamino$_{(C≤12)}$, substituted alkylamino$_{(C≤12)}$, dialkylamino$_{(C≤12)}$, substituted dialkylamino$_{(C≤12)}$, alkylsulfonyl$_{(C≤12)}$, substituted alkylsulfonyl$_{(C≤12)}$, alkylphosphate$_{(C≤12)}$, substituted alkylphosphate$_{(C≤12)}$, dialkylphosphate$_{(C≤12)}$, substituted dialkylphosphate$_{(C≤12)}$, or —C(O)$R_5$ wherein $R_5$ is alkoxy$_{(C≤12)}$ or substituted alkoxy$_{(C≤12)}$; $R_7$ is hydrogen, alkyl$_{(C≤12)}$, or substituted alkyl$_{(C≤12)}$; and m and n are each independently selected 0, 1, 2, 3, 4, 5, 6, 7, 8, 9, or 10; or a pharmaceutically acceptable salt or optical isomer thereof. In some embodiments, the compound is further defined by the formula:

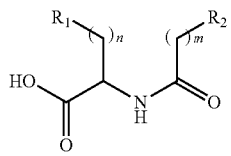
(IV)

wherein: $R_1$ and $R_2$ are each independently selected from amino, hydroxy, carboxy, guanidinyl, alkylguanidinyl$_{(C≤18)}$, substituted alkylguanidinyl$_{(C≤18)}$, urea, alkylurea$_{(C≤18)}$, substituted alkylurea$_{(C≤18)}$, boronic acid, boronic ester$_{(C≤18)}$, substituted boronic ester$_{(C≤18)}$, phosphate, sulfonyl, sulfinyl, mercapto, cyano, acyl$_{(C≤12)}$, substituted acyl$_{(C≤12)}$, amido$_{(C≤12)}$, substituted amido$_{(C≤12)}$, alkoxy$_{(C≤12)}$, substituted alkoxy$_{(C≤12)}$, alkylamino$_{(C≤12)}$, substituted alkylamino$_{(C≤12)}$, dialkylamino$_{(C≤12)}$, substituted dialkylamino$_{(C≤12)}$, alkylsulfonyl$_{(C≤12)}$, substituted alkylsulfonyl$_{(C≤12)}$, alkylphosphate$_{(C≤12)}$, substituted alkylphosphate$_{(C≤12)}$, dialkylphosphate$_{(C≤12)}$, substituted dialkylphosphate$_{(C≤12)}$, or —C(O)$R_5$ wherein $R_5$ is alkoxy$_{(C≤12)}$ or substituted alkoxy$_{(C≤12)}$; and m and n are each independently selected 1, 2, 3, 4, 5, 6, 7, 8, 9, or 10; or a pharmaceutically acceptable salt or optical isomer thereof. In some embodiments, the compound is further defined by the formula:

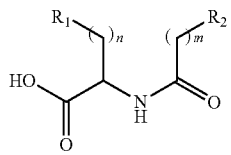
(IV)

wherein: $R_1$ and $R_2$ are each independently selected from amino, hydroxy, carboxy, guanidinyl, alkylguanidinyl$_{(C≤18)}$, substituted alkylguanidinyl$_{(C≤18)}$, urea, alkylurea$_{(C≤18)}$, substituted alkylurea$_{(C≤18)}$, alkylamino$_{(C≤12)}$, substituted alkylamino$_{(C≤12)}$, dialkylamino$_{(C≤12)}$, substituted dialkylamino$_{(C≤12)}$, or —C(O)$R_5$ wherein $R_5$ is alkoxy$_{(C≤12)}$ or substituted alkoxy$_{(C≤12)}$; and m and n are each independently selected 1, 2, 3, 4, 5, 6, 7, or 8; or a pharmaceutically acceptable salt or optical isomer thereof. In some embodiments, $R_1$ is amino. In other embodiments, $R_1$ is guanidinyl. In other embodiments, $R_1$ is urea. In some embodiments, $R_2$ is carboxy. In other embodiments, $R_2$ is amino. In some embodiments, $R_3$ is hydrogen. In some embodiments, $R_4$ is hydrogen. In some embodiments, $X_1$ is —C(O)$R_6$. In some embodiments, $R_6$ is alkoxy$_{(C≤12)}$ or substituted alkoxy$_{(C≤12)}$. In some embodiments, $R_6$ is —OCH$_3$. In some embodiments, $X_2$ is —C(O)—. In some embodiments, carbon 1 is in the R configuration. In other embodiments, carbon 1 is in the S configuration. In other embodiments, carbon 1 comprises a mixture of formulas in the R and S configuration. In some embodiments, m is 2, 3, 4, 5, 6, 7, or 8. In some embodiments, m is 2. In other embodiments, m is 4. In other embodiments, m is 5. In other embodiments, m is 6. In other embodiments, m is 7. In other embodiments, m is 8. In some embodiments, n is 2, 3, 4, 5, or 6. In some embodiments, n is 3. In other embodiments, n is 4. In some embodiments, $R_7$ is hydrogen. In some embodiments, the natural source is a toad skin extract. In some embodiments, the formula is not:

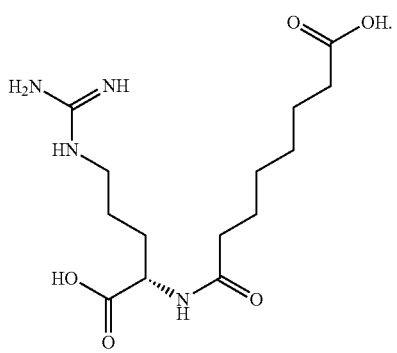 [SMILES: N=C(N)NCCC[C@H](NC(=O)CCCCCCC(=O)O)C(=O)O]
In some embodiments, $R_1$ is not guanidinyl, $R_2$ is not carboxyl, $R_3$ is not hydrogen, n is not 3 and m is not 6. In some embodiments, the compound is selected from the group consisting of:
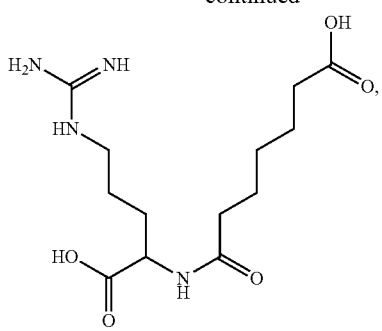
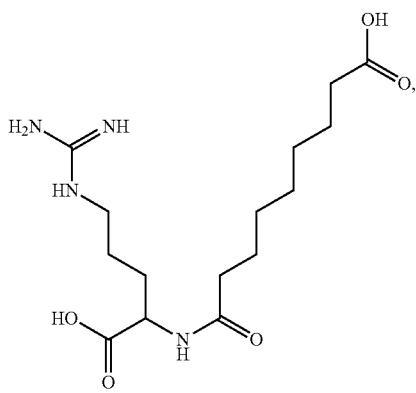
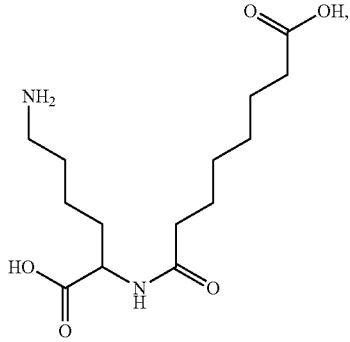
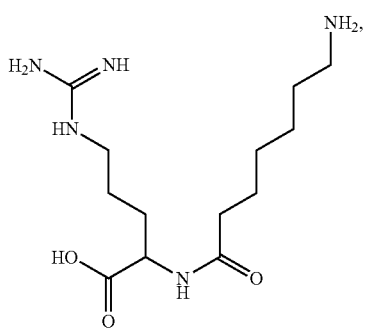
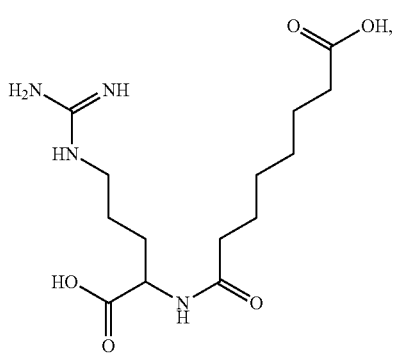

-continued
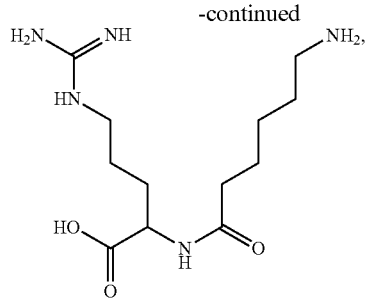
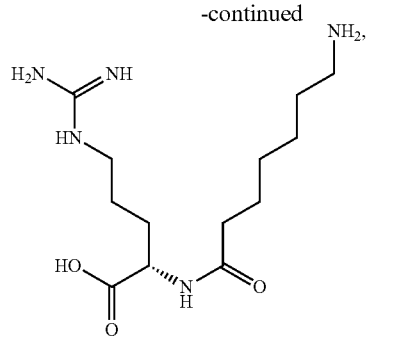
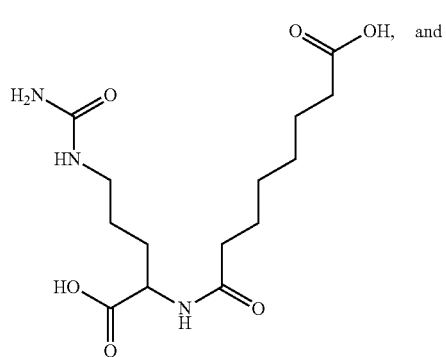
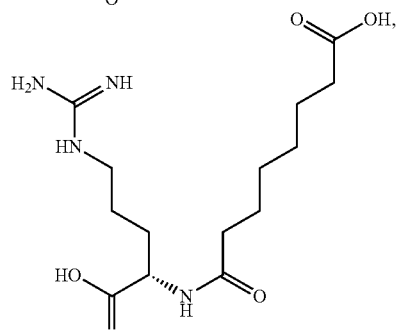
or a pharmaceutically acceptable salt or optical isomer thereof. In some embodiments, the compound is selected from the group consisting of:
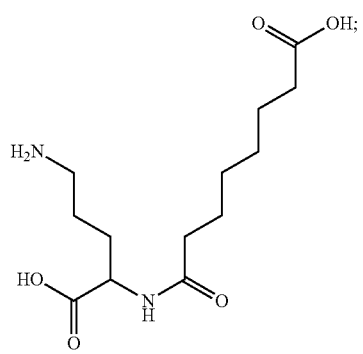 [SMILES: NCCCC(NC(=O)CCCCCCC(=O)O)C(=O)O]
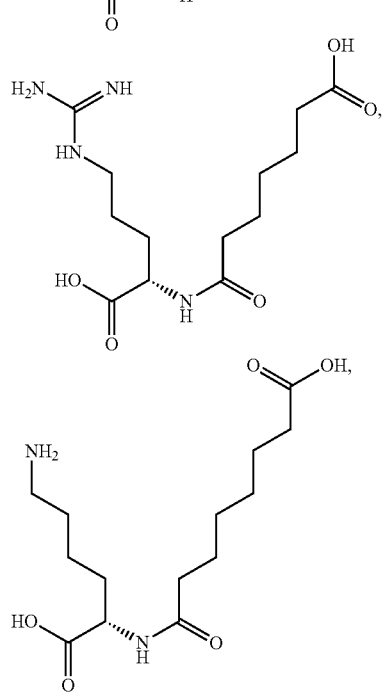
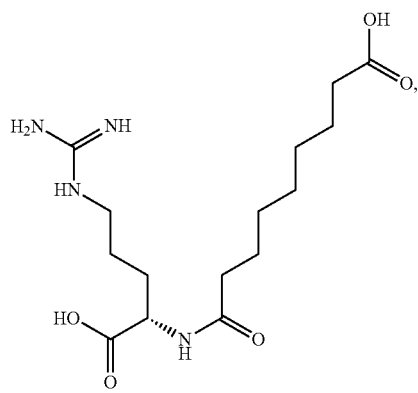
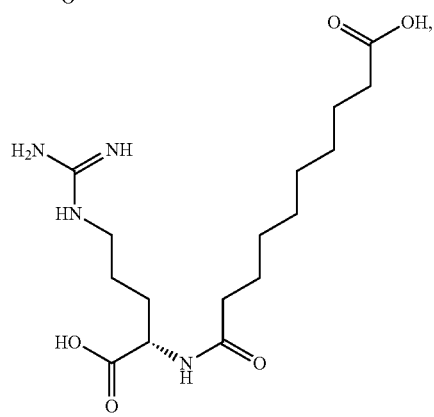

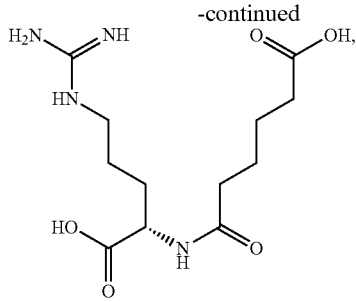

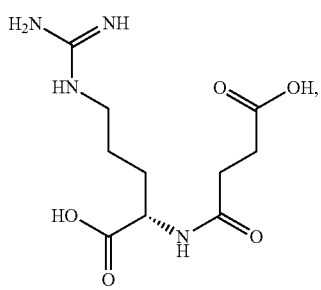

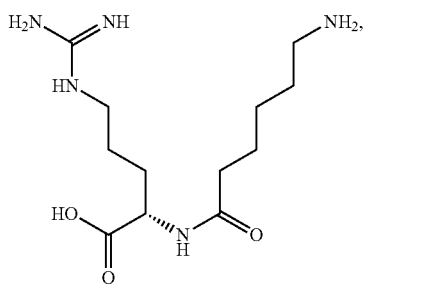

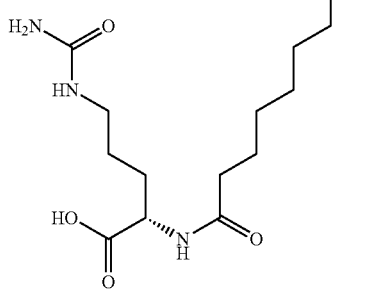

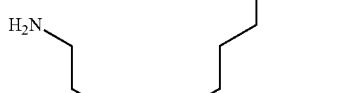

or a pharmaceutically acceptable salt thereof. In some embodiments, the compound is further defined as:

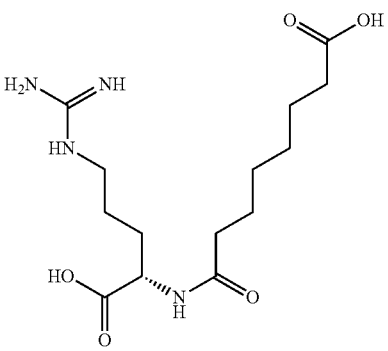

or a pharmaceutically acceptable salt thereof. In some embodiments, the compound is administered alone. In some embodiments, the compound is coadministered with a dose of erythropoietin. In some embodiments, the amount of the erythropoietin dose is decreased relative to the amount needed if erythropoietin is administered alone. In some embodiments, the coadministration of the compound with erythropoietin reduces the side effects of erythropoietin. In some embodiments, the substantially isolated or purified form comprises the compound separated away from the other components of the toad skin extract. In some embodiments, the compound comprises 80% of the total mass of the substantially isolated or purified form. In some embodiments, the compound comprises 90% of the total mass of the substantially isolated or purified form. In other embodiments, the compound is in a chemical synthesized form.

In yet another aspect, the present disclosure provides a method of promoting regeneration of hematopoietic stem cells in a patient comprising administering to the patient a pharmaceutically effective amount of a compound wherein the compound is chemically synthesized or is provided in a substantially isolated or purified form from a natural source and is of the formula:

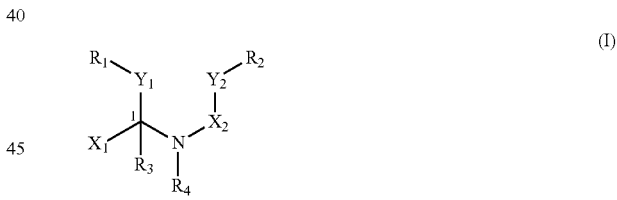

(I)

wherein: $R_1$ and $R_2$ are each independently selected from amino, hydroxy, carboxy, guanidinyl, alkylguanidinyl$_{(C \leq 18)}$, substituted alkylguanidinyl$_{(C \leq 18)}$, urea, alkylurea$_{(C \leq 18)}$, substituted alkylurea$_{(C \leq 18)}$, boronic acid, boronic ester$_{(C \leq 18)}$, substituted boronic ester$_{(C \leq 18)}$, phosphate, sulfonyl, sulfinyl, mercapto, cyano, acyl$_{(C \leq 12)}$, substituted acyl$_{(C \leq 12)}$, amido$_{(C \leq 12)}$, substituted amido$_{(C \leq 12)}$, alkoxy$_{(C \leq 12)}$, substituted alkoxy$_{(C \leq 12)}$, alkylamino$_{(C \leq 12)}$, substituted alkylamino$_{(C \leq 12)}$, dialkylamino$_{(C \leq 12)}$, substituted dialkylamino$_{(C \leq 12)}$, alkylsulfonyl$_{(C \leq 12)}$, substituted alkylsulfonyl$_{(C \leq 12)}$, alkylphosphate$_{(C \leq 12)}$, substituted alkylphosphate$_{(C \leq 12)}$, dialkylphosphate$_{(C \leq 12)}$, substituted dialkylphosphate$_{(C \leq 12)}$, or —C(O)R$_5$ wherein R$_5$ is alkoxy$_{(C \leq 12)}$ or substituted alkoxy$_{(C \leq 12)}$; $R_3$ and $R_4$ are each independently selected from hydrogen, alkyl$_{(C \leq 12)}$, or substituted alkyl$_{(C \leq 12)}$; or $R_3$ is taken together with $Y_2$ to form a cyclic structure comprising 5, 6, 7, 8, 9, 10, 11, or 12 atoms; $X_1$ is amino, carboxy, cyano, guanidinyl, hydroxy, mercapto, phosphate, phosphoamino, sulfinyl, sulfonyl, urea, —C(O)R$_6$, —C(NH)R$_6$, or —S(O)$_2$R$_6$ wherein R$_6$ is hydroxy; amino; alkoxy$_{(C≤12)}$; alkylamino$_{(C≤12)}$; dialkylamino$_{(C≤12)}$; or a substituted version of any of the last three groups, amido$_{(C≤12)}$, alkylsulfonyl$_{(C≤12)}$, alkylphosphate$_{(C≤12)}$, dialkylphosphate$_{(C≤12)}$, alkylphosphoamino$_{(C≤12)}$, dialkylphosphoamino$_{(C≤12)}$, or a substituted version of any of the last six groups; X$_2$ is —C(O)—, —C(NR')—, —NR'C(O)NR"—, —NR'C(S)NR"—, —NR'C(NR")NR'''—, —S(O)$_2$—, —S(O)$_2$NR'—, —NR'S(O)$_2$—, —P(O)(OR')—, —P(O)(NR'R")—, —(NR'R")P(O)—, —P(O)(OR')—, —P(O)(NR'R")—, —(NR'R")P(O)—, —OP(O)(OR')—, —P(O)(OR')O—, —P(O)(NR'R")O—, —OP(O)(NR'R")—, —NR'''(NR'R")P(O)—, —(NR'R")P(O)NR'''—, wherein R', R", and R''' are each independently hydrogen, alkyl$_{(C≤8)}$, or substituted alkyl$_{(C≤8)}$; Y$_1$ and Y$_2$ are each independently a covalent bond, alkanediyl$_{(C≤12)}$, alkenediyl$_{(C≤12)}$, alkynediyl$_{(C≤12)}$, arenediyl$_{(C≤12)}$, alkoxydiyl$_{(C≤12)}$, alkylaminodiyl$_{(C≤12)}$, or a substituted version of any of these groups; or when Y$_2$ is taken together with R$_3$ to form a cyclic structure comprising 5, 6, 7, 8, 9, 10, 11, or 12 atoms and Y$_2$ is alkanetriyl$_{(C≤12)}$, alkenetriyl$_{(C≤12)}$, alkynetriyl$_{(C≤12)}$, arenetriyl$_{(C≤12)}$, alkoxytriyl$_{(C≤12)}$, alkylaminotriyl$_{(C≤12)}$, or a substituted version of any of these groups; and carbon 1 is in the R configuration, S configuration, or a mixture thereof or a pharmaceutically acceptable salt or optical isomer thereof. In some embodiments, the compound is further defined as:

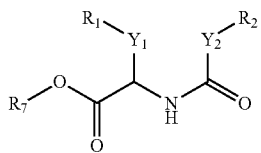
(II)

wherein: R$_1$ and R$_2$ are each independently selected from amino, hydroxy, carboxy, guanidinyl, alkylguanidinyl$_{(C≤18)}$, substituted alkylguanidinyl$_{(C≤18)}$, urea, alkylurea$_{(C≤18)}$, substituted alkylurea$_{(C≤18)}$, boronic acid, boronic ester$_{(C≤18)}$, substituted boronic ester$_{(C≤18)}$, phosphate, sulfonyl, sulfinyl, mercapto, cyano, acyl$_{(C≤12)}$, substituted acyl$_{(C≤12)}$, amido$_{(C≤12)}$, substituted amido$_{(C≤12)}$, alkoxy$_{(C≤12)}$, substituted alkoxy$_{(C≤12)}$, alkylamino$_{(C≤12)}$, substituted alkylamino$_{(C≤12)}$, dialkylamino$_{(C≤12)}$, substituted dialkylamino$_{(C≤12)}$, alkylsulfonyl$_{(C≤12)}$, substituted alkylsulfonyl$_{(C≤12)}$, alkylphosphate$_{(C≤12)}$, substituted alkylphosphate$_{(C≤12)}$, dialkylphosphate$_{(C≤12)}$, substituted dialkylphosphate$_{(C≤12)}$, or —C(O)R$_5$ wherein R$_5$ is alkoxy$_{(C≤12)}$ or substituted alkoxy$_{(C≤12)}$; R$_7$ is hydrogen, alkyl$_{(C≤12)}$, or substituted alkyl$_{(C≤12)}$; and Y$_1$ and Y$_2$ are each independently a covalent bond, alkanediyl$_{(C≤12)}$, alkenediyl$_{(C≤12)}$, alkynediyl$_{(C≤12)}$, arenediyl$_{(C≤12)}$, alkoxydiyl$_{(C≤12)}$, alkylaminodiyl$_{(C≤12)}$, or a substituted version of any of these groups; or a pharmaceutically acceptable salt or optical isomer thereof. In some embodiments, compound is further defined as:

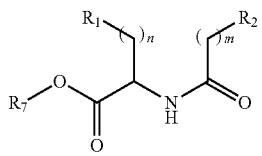
(III)

wherein: R$_1$ and R$_2$ are each independently selected from amino, hydroxy, carboxy, guanidinyl, alkylguanidinyl$_{(C≤18)}$, substituted alkylguanidinyl$_{(C≤18)}$, urea, alkylurea$_{(C≤18)}$, substituted alkylurea$_{(C≤18)}$, boronic acid, boronic ester$_{(C≤18)}$, substituted boronic ester$_{(C≤18)}$, phosphate, sulfonyl, sulfinyl, mercapto, cyano, acyl$_{(C≤12)}$, substituted acyl$_{(C≤12)}$, amido$_{(C≤12)}$, substituted amido$_{(C≤12)}$, alkoxy$_{(C≤12)}$, substituted alkoxy$_{(C≤12)}$, alkylamino$_{(C≤12)}$, substituted alkylamino$_{(C≤12)}$, dialkylamino$_{(C≤12)}$, substituted dialkylamino$_{(C≤12)}$, alkylsulfonyl$_{(C≤12)}$, substituted alkylsulfonyl$_{(C≤12)}$, alkylphosphate$_{(C≤12)}$, substituted alkylphosphate$_{(C≤12)}$, dialkylphosphate$_{(C≤12)}$, substituted dialkylphosphate$_{(C≤12)}$, or —C(O)R$_5$ wherein R$_5$ is alkoxy$_{(C≤12)}$ or substituted alkoxy$_{(C≤12)}$; R$_7$ is hydrogen, alkyl$_{(C≤12)}$, or substituted alkyl$_{(C≤12)}$; and m and n are each independently selected 0, 1, 2, 3, 4, 5, 6, 7, 8, 9, or 10; or a pharmaceutically acceptable salt or optical isomer thereof. In some embodiments, the compound is further defined by the formula:

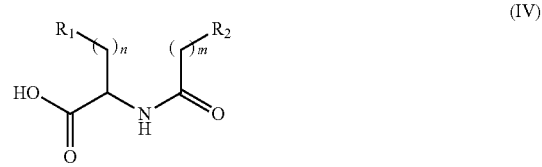
(IV)

wherein: R$_1$ and R$_2$ are each independently selected from amino, hydroxy, carboxy, guanidinyl, alkylguanidinyl$_{(C≤18)}$, substituted alkylguanidinyl$_{(C≤18)}$, urea, alkylurea$_{(C≤18)}$, substituted alkylurea$_{(C≤18)}$, boronic acid, boronic ester$_{(C≤18)}$, substituted boronic ester$_{(C≤18)}$, phosphate, sulfonyl, sulfinyl, mercapto, cyano, acyl$_{(C≤12)}$, substituted acyl$_{(C≤12)}$, amido$_{(C≤12)}$, substituted amido$_{(C≤12)}$, alkoxy$_{(C≤12)}$, substituted alkoxy$_{(C≤12)}$, alkylamino$_{(C≤12)}$, substituted alkylamino$_{(C≤12)}$, dialkylamino$_{(C≤12)}$, substituted dialkylamino$_{(C≤12)}$, alkylsulfonyl$_{(C≤12)}$, substituted alkylsulfonyl$_{(C≤12)}$, alkylphosphate$_{(C≤12)}$, substituted alkylphosphate$_{(C≤12)}$, dialkylphosphate$_{(C≤12)}$, substituted dialkylphosphate$_{(C≤12)}$, or —C(O)R$_5$ wherein R$_5$ is alkoxy$_{(C≤12)}$ or substituted alkoxy$_{(C≤12)}$; and m and n are each independently selected 1, 2, 3, 4, 5, 6, 7, 8, 9, or 10; or a pharmaceutically acceptable salt or optical isomer thereof. In some embodiments, the compound is further defined by the formula:

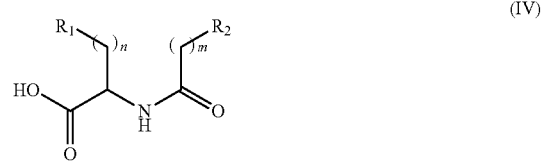
(IV)

wherein: R$_1$ and R$_2$ are each independently selected from amino, hydroxy, carboxy, guanidinyl, alkylguanidinyl$_{(C≤18)}$, substituted alkylguanidinyl$_{(C≤18)}$, urea, alkylurea$_{(C≤18)}$, substituted alkylurea$_{(C≤18)}$, alkylamino$_{(C≤12)}$, substituted alkylamino$_{(C≤12)}$, dialkylamino$_{(C≤12)}$, substituted dialkylamino$_{(C≤12)}$, or —C(O)R$_5$ wherein R$_5$ is alkoxy$_{(C≤12)}$ or substituted alkoxy$_{(C≤12)}$; and m and n are each independently selected 1, 2, 3, 4, 5, 6, 7, or 8; or a pharmaceutically acceptable salt or optical isomer thereof. In some embodiments, R$_1$ is amino. In other embodiments, R$_1$ is guanidinyl. In other embodiments, R$_1$ is urea. In some embodiments, R$_2$ is carboxy. In other embodiments, R$_2$ is amino. In some embodiments, $R_3$ is hydrogen. In some embodiments, $R_4$ is hydrogen. In some embodiments, $X_1$ is —C(O)$R_6$. In some embodiments, $R_6$ is alkoxy$_{(C≤12)}$ or substituted alkoxy$_{(C≤12)}$. In some embodiments, $R_6$ is —OCH$_3$. In some embodiments, $X_2$ is —C(O)—. In some embodiments, carbon 1 is in the R configuration. In other embodiments, carbon 1 is in the S configuration. In other embodiments, carbon 1 comprises a mixture of formulas in the R and S configuration. In some embodiments, m is 2, 3, 4, 5, 6, 7, or 8. In some embodiments, m is 2. In other embodiments, m is 4. In other embodiments, m is 5. In other embodiments, m is 6. In other embodiments, m is 7. In other embodiments, m is 8. In some embodiments, n is 2, 3, 4, 5, or 6. In some embodiments, n is 3. In other embodiments, n is 4. In some embodiments, $R_2$ is hydrogen. In some embodiments, the natural source is a toad skin extract. In some embodiments, the formula is not:

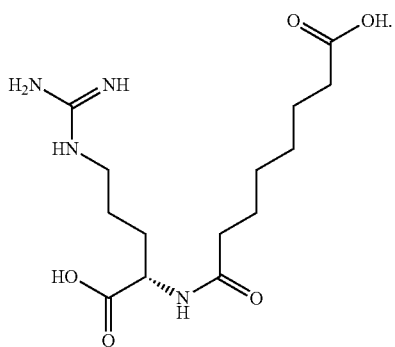 [SMILES: N=C(N)NCCC[C@H](NC(=O)CCCCCCC(=O)O)C(=O)O]

In some embodiments, $R_1$ is not guanidinyl, $R_2$ is not carboxyl, $R_3$ is not hydrogen, n is not 3 and m is not 6. In some embodiments, the compound is selected from the group consisting of:

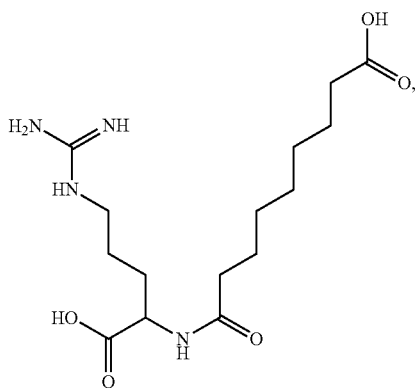

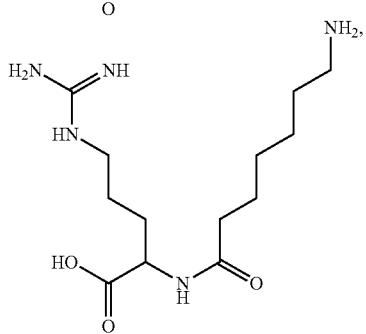

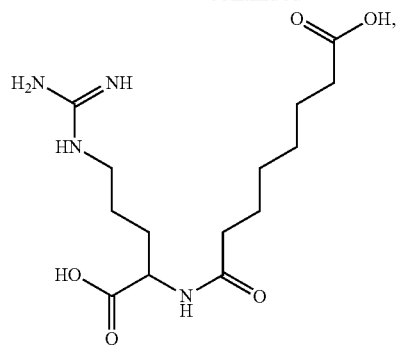

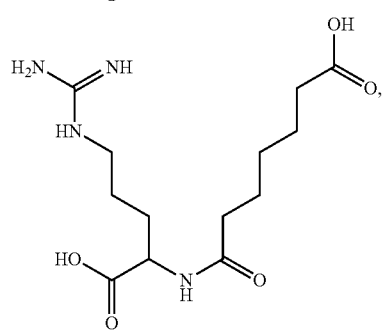

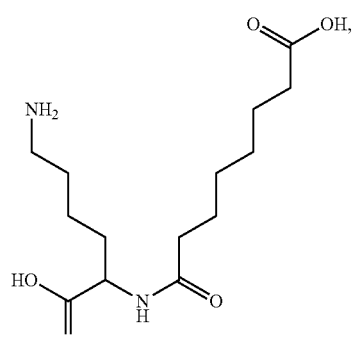

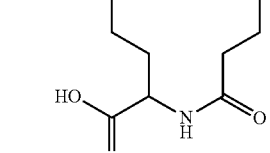

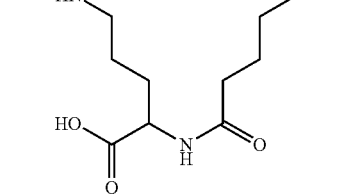

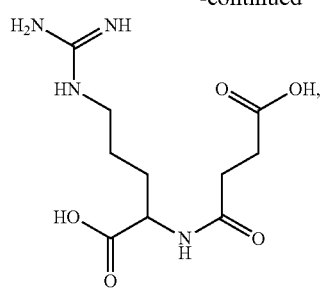
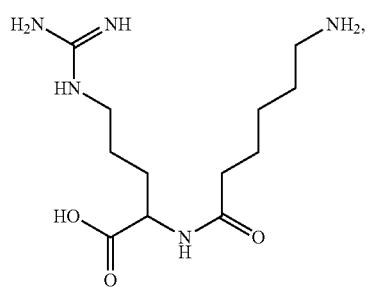
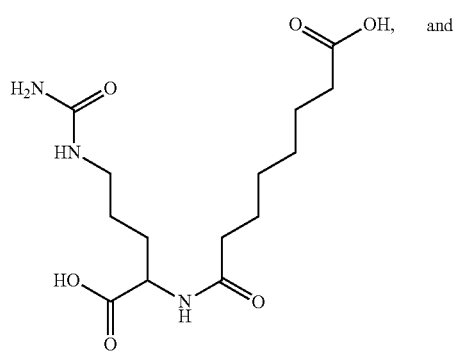
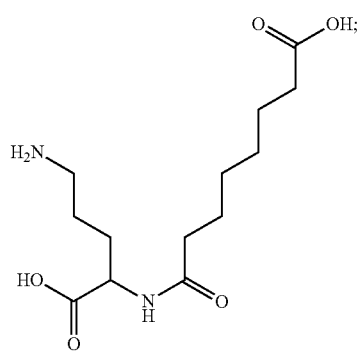
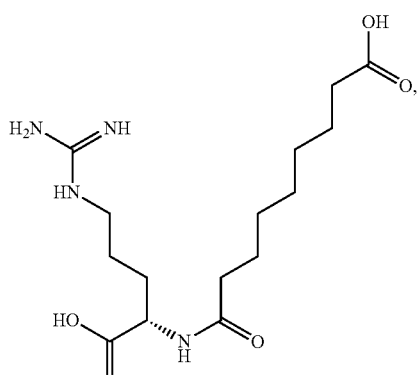
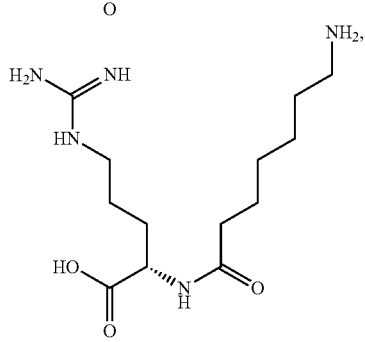
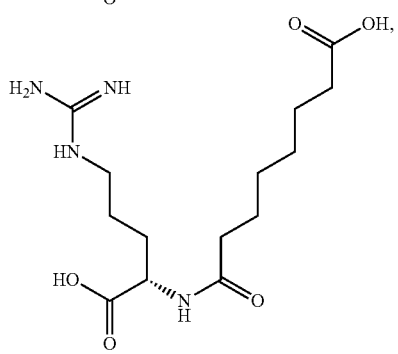
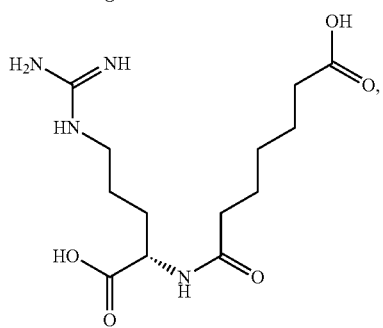
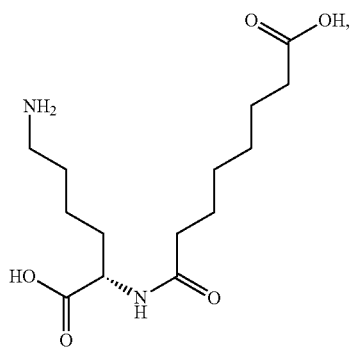
and
or a pharmaceutically acceptable salt or optical isomer thereof. In some embodiments, the compound is selected from the group consisting of:

-continued

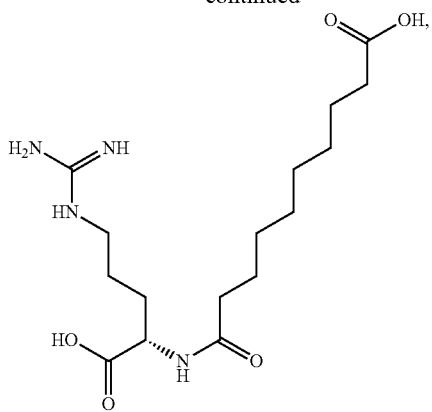

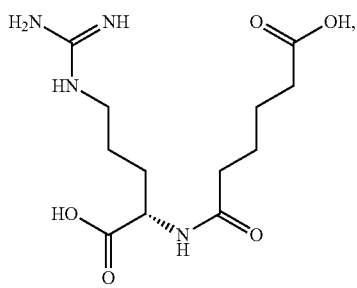

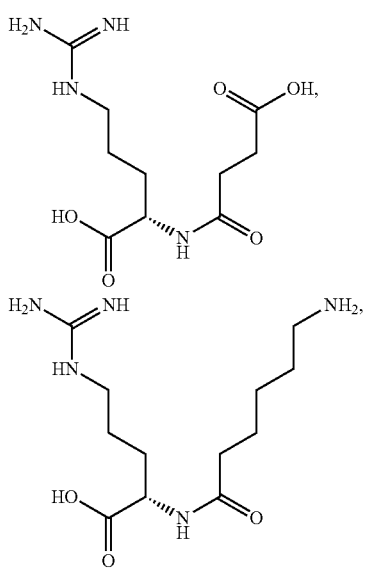

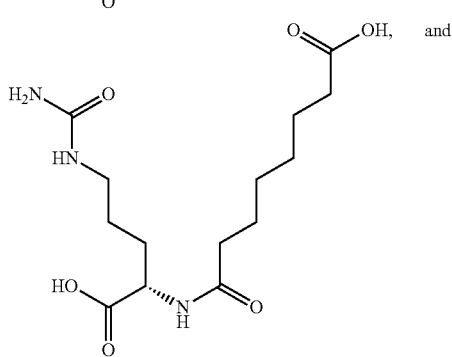

-continued

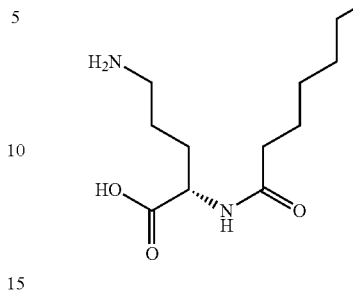

or a pharmaceutically acceptable salt thereof. In some embodiments, the compound is further defined as:

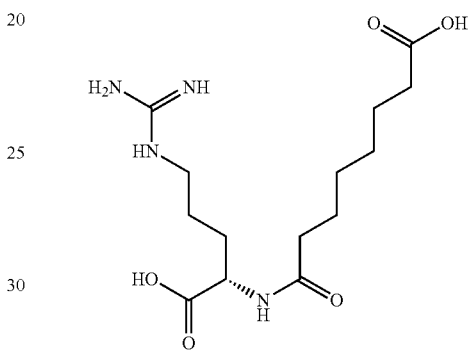

or a pharmaceutically acceptable salt thereof. In some embodiments, the regeneration of hematopoietic stem cells occurs in vivo. In some embodiments, the regeneration of hematopoietic stem cells results in an increase in red blood cells. In some embodiments, the regeneration of hematopoietic stem cells is sufficient to effectively treat a patient with a deficiency in red blood cells. In some embodiments, the deficiency in red blood cells is due to a decrease in the production of red blood cells. In some embodiments, the compound is administered with a surgery or second drug known to decrease the production of red blood cells. In some embodiments, the compound is coadministered with the second drug selected from a chemotherapeutic agent, a radiotherapeutic agent, atovaquone, azacitidine, bexarotene, boceprevir, bosentan, bosutinib, brentuximab vedotin, carbidopa-levodopa, carglumic acid, decitabine, eribulin mesylate, foscarnet, metformin, ofatumumab, pomalidomide, prelatrexate solution, ropivacaine, rosiglitazone, sirolimus, temsirolimus, and valganciclovir. In some embodiments, the compound mitigates or prevents the decrease in the production of red blood cells caused by the surgery or second drug. In some embodiments, the substantially isolated or purified form comprises the compound separated away from the other components of the toad skin extract. In some embodiments, the compound comprises 80% of the total mass of the substantially isolated or purified form. In some embodiments, the compound comprises 90% of the total mass of the substantially isolated or purified form. In other embodiments, the compound is in a chemical synthesized form.

The term "effective," as that term is used in the specification and/or claims (e.g., "an effective amount," means adequate to accomplish a desired, expected, or intended result.

"Treatment" and "treating" as used herein refer to administration or application of a therapeutic agent to a subject or performance of a procedure or modality on a subject for the purpose of obtaining a therapeutic benefit of a disease or health-related condition. For example, a subject (e.g., a mammal, such as a human) having a bacterial infection may be subjected to a treatment comprising administration of a compound of the present disclosure.

The term "therapeutic benefit" or "therapeutically effective" as used throughout this application refers to anything that promotes or enhances the well-being of the subject with respect to the medical treatment of a condition. This includes, but is not limited to, a reduction in the frequency or severity of the signs or symptoms of a disease. For example, a therapeutically effective amount of a compound of the present disclosure may be administered to a subject having a bacterial infection, such that the infection is mitigated or eliminated.

The term "substantially isolated or purified" as used throughout this application refers to a compound which has been substantially purified away from the other components of toad skin extract. Furthermore, in some embodiments of the present disclosure, "substantially isolated or purified" means the compound has been separated or purified away from any of the toxic components. In some embodiments, "substantially isolated or purified" means greater than 80% of the total mass is the active compound. In some embodiments, "substantially isolated or purified" means greater than 90% of the total mass is the active compound. In some embodiments, "substantially isolated or purified" means greater than 95% of the total mass is the active compound. In some embodiments, "substantially isolated or purified" means that the compound has been chemically synthesized rather than obtained from the toad skin extract.

It is specifically contemplated that any limitation discussed with respect to one embodiment of the disclosure may apply to any other embodiment of the disclosure. Furthermore, any composition of the disclosure may be used in any method of the disclosure, and any method of the disclosure may be used to produce or to utilize any composition of the disclosure.

The use of the term "or" in the claims is used to mean "and/or" unless explicitly indicated to refer to alternatives only or the alternative are mutually exclusive, although the disclosure supports a definition that refers to only alternatives and "and/or."

Throughout this application, the term "about" is used to indicate that a value includes the standard deviation of error for the device and/or method being employed to determine the value.

As used herein the specification, "a" or "an" may mean one or more, unless clearly indicated otherwise. As used herein in the claim(s), when used in conjunction with the word "comprising," the words "a" or "an" may mean one or more than one. As used herein "another" may mean at least a second or more.

Other objects, features and advantages of the present disclosure will become apparent from the following detailed description. It should be understood, however, that the detailed description and the specific examples, while indicating particular embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The following figures form part of the present specification and are included to further demonstrate certain aspects of the present disclosure. The disclosure may be better understood by reference to one or more of these drawings in combination with the detailed description of specific embodiments presented herein.

(FIG. 7A) SA is metabolically stable in S9 liver fractions. SA (2 µM) was incubated with murine S9 (Lot KWB) and Phase I NADPH Regenerating System cofactors for 0-240 minutes. SA was quantified using a Qtrap 3200 mass spectrometer. n=3. (FIG. 7B) SA is stable in mouse plasma. 1 µl SA 2 mM DMSO stock was incubated with 1 ml ACD mouse plasma or saline making 2 µM SW125991 working solution. Vortext well and incubate in 37° C. water bath. At time point 0, 10, 30, 60, 120, 240, 1440 min, SA was quantified using a Qtrap 3200 mass spectrometer. n=3.

DESCRIPTION OF ILLUSTRATIVE EMBODIMENTS

Figure 1A:
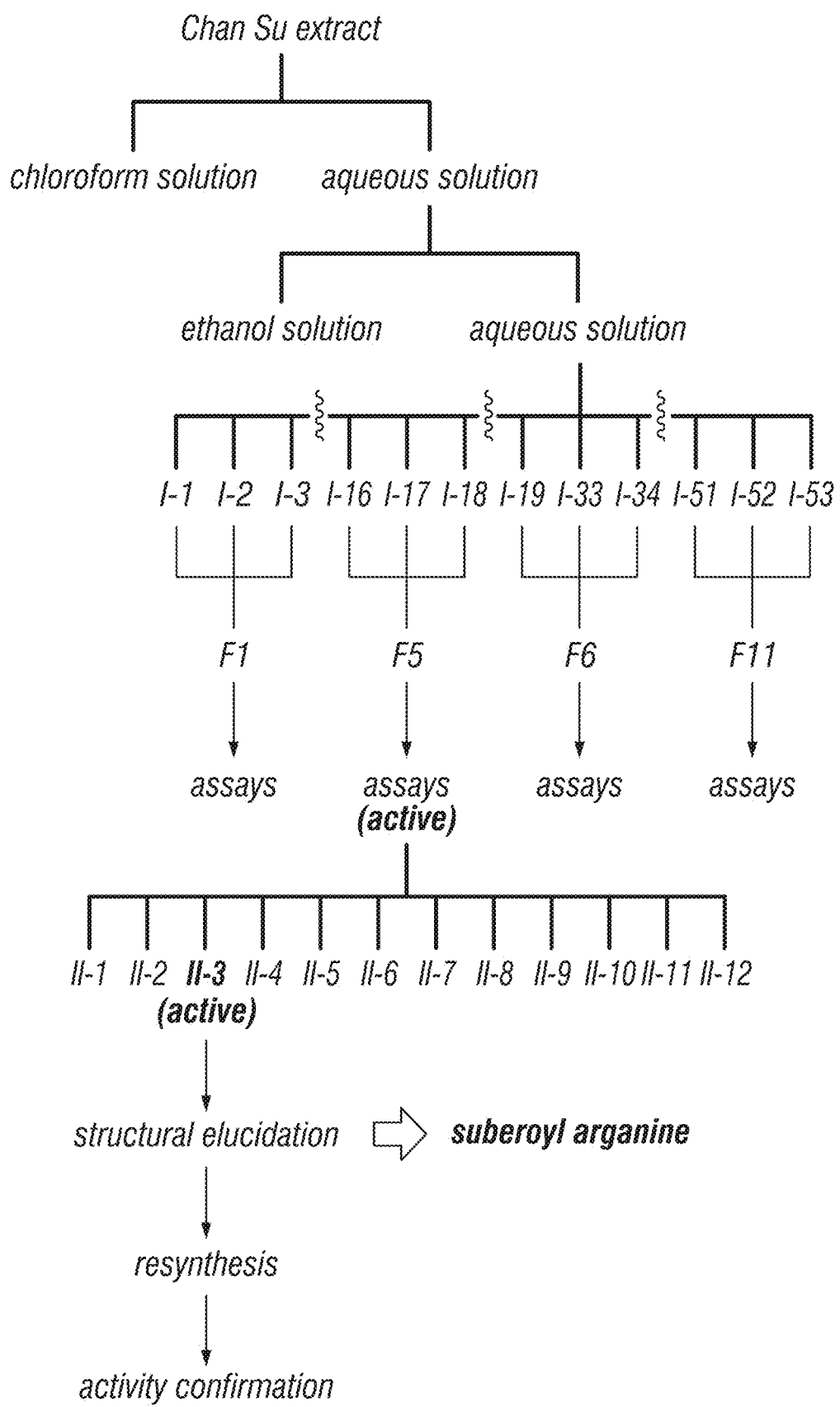
FIG. 1A shows the isolation of SA from the Chan Su extract that supports hematopoietic regeneration. Schematic of fractionation and functional assays.

The present disclosure relates to compounds which increases the recovery of red blood cells and hematopoietic stem cells. A toad extract has been used in China to treat diseases such as anemia and red blood cell deficiency without any knowledge of the specific compound responsible for the beneficial properties. The isolated compound, subreoylarginine, and its deriviatives described herein can promote the recovery of red blood cells and hematopoietic stem cells in vivo. Currently, the only medicine commercially available for increasing the proliferation of red blood cells is erthyropoietin, but erthyropoietin causes severe side effects such as hypertension, cardiovascular disease, or cancer. The compounds reported in this disclosure are the first known isolated individual compounds to stimulate hematopoietic stem cells and lead to the proliferation of red blood cells.

A. COMPOUNDS OF THE PRESENT DISCLOSURE

In some embodiments of the present disclosure, the disclosure relates to compounds of the formula:

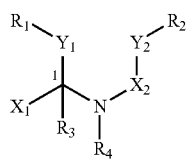

(I)

wherein: $R_1$ and $R_2$ are each independently selected from amino, hydroxy, carboxy, guanidinyl, alkylguanidinyl$_{(C \leq 18)}$, substituted alkylguanidinyl$_{(C \leq 18)}$, urea, alkylurea$_{(C \leq 18)}$, substituted alkylurea$_{(C \leq 18)}$, boronic acid, boronic ester$_{(C \leq 18)}$, substituted boronic ester$_{(C \leq 18)}$, phosphate, sulfonyl, sulfinyl, mercapto, cyano, acyl$_{(C \leq 12)}$, substituted acyl$_{(C \leq 12)}$, amido$_{(C \leq 12)}$, substituted amido$_{(C \leq 12)}$, alkoxy$_{(C \leq 12)}$, substituted alkoxy$_{(C \leq 12)}$, alkylamino$_{(C \leq 12)}$, substituted alkylamino$_{(C \leq 12)}$, dialkylamino$_{(C \leq 12)}$, substituted dialkylamino$_{(C \leq 12)}$, alkylsulfonyl$_{(C \leq 12)}$, substituted alkylsulfonyl$_{(C \leq 12)}$, alkylphosphate$_{(C \leq 12)}$, substituted alkylphosphate$_{(C \leq 12)}$, dialkylphosphate$_{(C \leq 12)}$, substituted dialkylphosphate$_{(C \leq 12)}$, or —C(O)R$_5$ wherein R$_5$ is alkoxy$_{(C \leq 12)}$ or substituted alkoxy$_{(C \leq 12)}$; R$_3$ and R$_4$ are each independently selected from hydrogen, alkyl$_{(C \leq 12)}$, or substituted alkyl$_{(C \leq 12)}$; or R$_3$ is taken together with Y$_2$ to form a cyclic structure comprising 5, 6, 7, 8, 9, 10, 11, or 12 atoms; X$_1$ is amino, carboxy, cyano, guanidinyl, hydroxy, mercapto, phosphate, phosphoamino, sulfinyl, sulfonyl, urea, —C(O)R$_6$, —C(NH)R$_6$, or —S(O)$_2$R$_6$ wherein R$_6$ is hydroxy; amino; alkoxy$_{(C \leq 12)}$; alkylamino$_{(C \leq 12)}$; dialkylamino$_{(C \leq 12)}$; or a substituted version of any of the last three groups, amido$_{(C \leq 12)}$, alkylsulfonyl$_{(C \leq 12)}$, alkylphosphate$_{(C \leq 12)}$, dialkylphosphate$_{(C \leq 12)}$, alkylphosphoamino$_{(C \leq 12)}$, dialkylphosphoamino$_{(C \leq 12)}$ or a substituted version of any of the last six groups; X$_2$ is —C(O)—, —C(NR')—, —NR'C(O)NR"—, —NR'C(S)NR"—, —NR'C(NR")NR'"—, —S(O)$_2$—, —S(O)$_2$NR'—, —NR'S(O)$_2$—, —P(O)(OR')—, —P(O)(NR'R")—, —(NR'R")P(O)—, —P(O)(OR')—, —P(O)(NR'R")—, —(NR'R")P(O)—, —OP(O)(OR')—, —P(O)(OR')O—, —P(O)(NR'R")O—, —OP(O)(NR'R")—, —NR'"(NR'R")P(O)—, —(NR'R")P(O)NR'"—, wherein R', R", and R'" are each independently hydrogen, alkyl$_{(C \leq 8)}$, or substituted alkyl$_{(C \leq 8)}$; Y$_1$ and Y$_2$ are each independently a covalent bond, alkanediyl$_{(C \leq 12)}$, alkenediyl$_{(C \leq 12)}$, alkynediyl$_{(C \leq 12)}$, arenediyl$_{(C \leq 12)}$, alkoxydiyl$_{(C \leq 12)}$, alkylaminodiyl$_{(C \leq 12)}$, or a substituted version of any of these groups; or when Y$_2$ is taken together with R$_3$ to form a cyclic structure comprising 5, 6, 7, 8, 9, 10, 11, or 12 atoms and Y$_2$ is alkanetriyl$_{(C \leq 12)}$, alkenetriyl$_{(C \leq 12)}$, alkynetriyl$_{(C \leq 12)}$, arenetriyl$_{(C \leq 12)}$, alkoxytriyl$_{(C \leq 12)}$, alkylaminotriyl$_{(C \leq 12)}$, or a substituted version of any of these groups; and carbon 1 is in the R configuration, S configuration, or a mixture thereof; or a salt or optical isomer thereof.

The compounds provided by the present disclosure are shown, for example, above in the summary of the disclosure section and in the claims below. They may be made using the conventional organic chemistry methods outlined in the Examples section (e.g., Example 1). These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein. Solvent choices for the methods of making compounds of the present disclosure will be known to one of ordinary skill in the art. Solvent choices may depend, for example, on which one(s) will facilitate the solubilizing of all the reagents or, for example, which one(s) will best facilitate the desired reaction (particularly when the mechanism of the reaction is known). Solvents may include, for example, polar solvents and non-polar solvents. Different types of organic solvents include, but are not limited to, tetrahydrofuran, dimethylformamide, dimethylsulfoxide, dioxane, methanol, ethanol, hexane, methylene chloride and acetonitrile. More than one solvent may be chosen for any particular reaction or purification procedure. Water may also be admixed into any solvent choice. Further, water, such as distilled water, may constitute the solvent instead of an organic solvent.

Persons of ordinary skill in the art, having been apprised of the active agents, will be able to purify such compounds by applying appropriate well known procedures. One of ordinary skill in the art will understand that compounds of the present disclosure can generally be purified at any step, including the purification of intermediates as well as purification of the final products. In particular embodiments, purification is performed via silica gel column chromatography, TLC, or HPLC using a bonded stationary phase.

In addition, atoms making up the compounds of the present disclosure are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}$C and $^{14}$C. Similarly, it is contemplated that one or more carbon atom(s) of a compound of the present disclosure may be replaced by a silicon atom(s). Furthermore, it is contemplated that one or more oxygen atom(s) of a compound of the present disclosure may be replaced by a sulfur or selenium atom(s).

The term "functional group" generally refers to how persons of skill in the art classify chemically reactive groups. Examples of functional groups include hydroxyl, amine, sulfhydryl, amide, carboxyls, carbonyls, etc.

As used herein, "protecting group" refers to a moiety attached to a functional group to prevent an otherwise unwanted reaction of that functional group. Protecting groups are well-known to those of skill in the art. Non-limiting exemplary protecting groups fall into categories such as hydroxy protecting groups, amino protecting groups, sulfhydryl protecting groups and carbonyl protecting groups. Such protecting groups may be found in Greene and Wuts, 1999, which is incorporated herein by reference. Compounds of the present disclosure are specifically contemplated wherein one or more functional groups are protected by a protecting group.

Modifications or derivatives of the compounds, agents, and active ingredients disclosed throughout this specification are contemplated as being useful with the methods and compositions of the present disclosure. Derivatives may be prepared and the properties of such derivatives may be assayed for their desired properties by any method known to those of skill in the art.

In certain aspects, "derivative" refers to a chemically modified compound that still retains the desired effects of the compound prior to the chemical modification ("the parent compound"). Such effects may be enhanced (e.g., slightly more effective, twice as effective, etc.) or diminished (e.g., slightly less effective, 2-fold less effective, etc.) relative to the parent compound, but may still be considered a derivative. Such derivatives may have the addition, removal, or substitution of one or more chemical moieties on the parent molecule. Non-limiting examples of the types of modifications that can be made to the compounds and structures disclosed herein include the addition or removal of lower unsubstituted alkyls such as methyl, ethyl, propyl, or substituted lower alkyls such as hydroxymethyl or aminomethyl groups; carboxyl groups and carbonyl groups; hydroxyls; nitro, amino, amide, imide and azo groups; sulfate, sulfonate, sulfono, sulfhydryl, sulfenyl, sulfonyl, sulfoxido, sulfonamido, phosphate, phosphono, phosphoryl groups, and halide substituents. Additional modifications can include an addition or a deletion of one or more atoms of the atomic framework, for example, substitution of an ethyl by a propyl; substitution of a phenyl by a larger or smaller aromatic group. Alternatively, in a cyclic or bicyclic structure, heteroatoms such as N, S, or O can be substituted into the structure instead of a carbon atom.

Prodrugs and solvates of the compounds of the present disclosure are also contemplated herein. The term "prodrug" as used herein, is understood as being a compound which, upon administration to a subject, such as a mammal, undergoes chemical conversion by metabolic or chemical processes to yield a compound any of the formulas herein, or a salt and/or solvate thereof (Bundgaard, 1991; Bundgaard, 1985). Solvates of the compounds of the present disclosure are preferably hydrates.

B. DEFICIENCIES IN RED BLOOD CELLS

The present disclosure relates to compounds which are known to promote the regeneration of red blood cells or hematopoietic stem cells which can be used to treat deficiencies in red blood cells. In some embodiments, the deficiency in red blood cells is an anemia. Anemia can result from two major causes: (i) a decrease in the production of red blood cells or (ii) an increase in the destruction of red blood cells. Additionally, anemia can be caused by blood loss or a fluid overload. In some embodiments, the present disclosure relates to compound which can be used to treat either a decrease in the production of red blood cells or an increase in the destruction of red blood cells. Furthermore, a red blood cell deficiency may be caused by the failure of the bone marrow to produce enough blood cells. In some embodiments, bone marrow failure results from an insufficient amount or potency of hematopoietic stem cells. Hematopoietic stem cells are a heterogeneous class of cells which give rise to all other blood cells including both the myeloid and lymphoid lineages. In some aspects, the compounds of the present disclosure may promote the regeneration of hematopoietic stem cells. In some aspects, hematopoietic stem cells are classified into three classes, myeloid-based, lymphoid-based and balanced hematopoietic stem cells which are affected equally by the compounds of the present disclosure. In some embodiments, one or more of these classes are affected more significantly than the other classes by the compound of the present disclosure.

Numerous diseases are associated with a decrease in the production or an increased destruction of the red blood cells. In particular, anemia is commonly associated with advanced stage or chronic kidney disease as the kidneys produces the protein, erythropoietin, which stimulates bone marrow to produce red blood cells. Additionally, in some aspects, cancer or HIV/AIDS can lead to a decrease in red blood cells. Furthermore, the method of treating the disease may also lead to anemia. In some embodiments, chemotherapeutic agents or radiation therapy have also been found to inhibit the formation of new blood cells and can lead to anemia. Finally, inflammatory diseases, such as, but not limited to, diabetes, lupus, rheumatoid arthritis and Crohn's disease, have been known to cause anemia. Without being bound by theory, inflammatory diseases are believed to cause anemia by interrupting the body's ability to absorb or utilize iron. Decreases in the body's ability to absorb or utilize iron in turn leads to decreased hemoglobin production. In some embodiments, inflammatory processes cause anemia by preventing the release of iron stores or decreasing the production of the protein associated with iron release. Additionally, inflammatory process may also cause anemia by decreasing the efficacy of the protein, erythropoietin. Since anemia may be caused both by disease or by the treatment of disease, the exact cause of anemia can be difficult to diagnosis. As such, the treatment of anemia is challenging since a single cause is often difficult to ascertain. Thus, therapeutic agents that can stimulate the production of red blood cells may be useful in treating a wide range of anemia irregardless of the anemia's cause.

C. CHEMICAL DEFINITIONS

When used in the context of a chemical group: "hydrogen" means —H; "hydroxy" means —OH; "oxo" means =O; "carbonyl" means —C(=O)—; "carboxy" means —C(=O)OH (also written as —COOH or —CO$_2$H); "halo" means independently —F, —Cl, —Br or —I; "amino" means —NH$_2$; "hydroxyamino" means —NHOH; "nitro" means —NO$_2$; imino means =NH; "urea" means —NHC(=O)NH$_2$; "guanidinyl" means —NHC(=NH)NH$_2$; "cyano" means —CN; "isocyanate" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "phosphoamino" means —NHP(O)(OH)$_2$ or —OP(O)(OH)(NH$_2$) "mercapto" means —SH; and "thio" means =S; "sulfonyl" means —S(O)$_2$—; and "sulfinyl" means —S(O)—.

In the context of chemical formulas, the symbol "—" means a single bond, "=" means a double bond, and "≡" means triple bond. The symbol "----" represents an optional bond, which if present is either single or double. The symbol "⎓" represents a single bond or a double bond. Thus, for example, the formula

includes

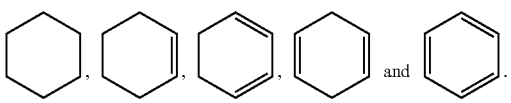

And it is understood that no one such ring atom forms part of more than one double bond. Furthermore, it is noted that the covalent bond symbol "—", when connecting one or two stereogenic atoms, does not indicate any preferred stereochemistry. Instead, it covers all stereoisomers as well as mixtures thereof. The symbol " ", when drawn perpendicularly across a bond (e.g.,

for methyl) indicates a point of attachment of the group. It is noted that the point of attachment is typically only identified in this manner for larger groups in order to assist the reader in unambiguously identifying a point of attachment. The symbol " " means a single bond where the group attached to the thick end of the wedge is "out of the page." The symbol " " means a single bond where the group attached to the thick end of the wedge is "into the page". The symbol " " means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a group "R" is depicted as a "floating group" on a ring system, for example, in the formula:

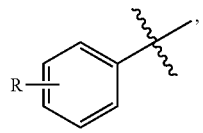

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

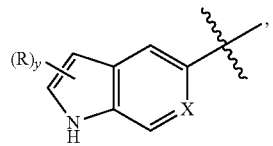

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the groups and classes below, the following parenthetical subscripts further define the group/class as follows: "(Cn)" defines the exact number (n) of carbon atoms in the group/class. "(C≤n)" defines the maximum number (n) of carbon atoms that can be in the group/class, with the minimum number as small as possible for the group in question, e.g., it is understood that the minimum number of carbon atoms in the group "alkenyl$_{(C≤8)}$" or the class "alkene$_{(C≤8)}$" is two. For example, "alkoxy$_{(C≤10)}$" designates those alkoxy groups having from 1 to 10 carbon atoms. (Cn-n') defines both the minimum (n) and maximum number (n') of carbon atoms in the group. Similarly, "alkyl$_{(C2-10)}$" designates those alkyl groups having from 2 to 10 carbon atoms.

The term "saturated" as used herein means the compound or group so modified has no carbon-carbon double and no carbon-carbon triple bonds, except as noted below. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkynes/alkynyl).

The term "alkyl" when used without the "substituted" modifier refers to a monovalent saturated aliphatic group with a carbon atom as the point of attachment, a linear or branched, cyclo, cyclic or acyclic structure, and no atoms other than carbon and hydrogen. Thus, as used herein cycloalkyl is a subset of alkyl, with the carbon atom that forms the point of attachment also being a member of one or more non-aromatic ring structures wherein the cycloalkyl group consists of no atoms other than carbon and hydrogen. As used herein, the term does not preclude the presence of one or more alkyl groups (carbon number limitation permitting) attached to the ring or ring system. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), —CH$_2$C(CH$_3$)$_3$ (neo-pentyl), cyclobutyl, cyclopentyl, cyclohexyl, and cyclohexylmethyl are non-limiting examples of alkyl groups. The term "alkanediyl" when used without the "substituted" modifier refers to a divalent saturated aliphatic group, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH$_2$-(methylene), —CH$_2$CH$_2$—, —CH$_2$C(CH$_3$)$_2$CH$_2$—, —CH$_2$CH$_2$CH$_2$—, and

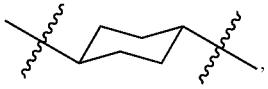 [SMILES: *C1CCC(*)CC1]

are non-limiting examples of alkanediyl groups. The term "alkanetriyl" when used without the "substituted" modifier refers to a trivalent saturated aliphatic group, with one, two, or three saturated carbon atom(s) as the point(s) of attachment, a linear or branched, cyclo, cyclic or acyclic structure, no carbon-carbon double or triple bonds, and no atoms other than carbon and hydrogen. The term "alkylidene" when used without the "substituted" modifier refers to the divalent group =CRR' in which R and R' are independently hydrogen, alkyl, or R and R' are taken together to represent an alkanediyl having at least two carbon atoms. Non-limiting examples of alkylidene groups include: =CH$_2$, =CH(CH$_2$CH$_3$), and =C(CH$_3$)$_2$. An "alkane" refers to the compound HR, wherein R is alkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which one or more hydrogen atoms has been substituted with a halo group and no other atoms aside from carbon, hydrogen and halogen are present. The group, —CH$_2$Cl is a non-limiting example of a haloalkyl. The term "fluoroalkyl" is a subset of substituted alkyl, in which one or more hydrogen has been substituted with a fluoro group and no other atoms aside from carbon, hydrogen and fluorine are present. The groups, —CH$_2$F, —CF$_3$, and —CH$_2$CF$_3$ are non-limiting examples of fluoroalkyl groups.

The term "alkenyl" when used without the "substituted" modifier refers to an monovalent unsaturated aliphatic group with a carbon atom as the point of attachment, a linear or branched, cyclo, cyclic or acyclic structure, at least one nonaromatic carbon-carbon double bond, no carbon-carbon triple bonds, and no atoms other than carbon and hydrogen. Non-limiting examples of alkenyl groups include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CHCH=CH$_2$. The term "alkenediyl" when used without the "substituted" modifier refers to a divalent unsaturated aliphatic group, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, —CH=CH, —CH=C(CH$_3$)CH$_2$—, —CH=CHCH$_2$, and

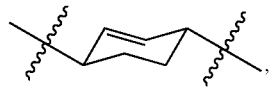 [SMILES: *C1C=CC(*)CC1]

are non-limiting examples of alkenediyl groups. The term "alkenediyl" when used without the "substituted" modifier refers to a trivalent unsaturated aliphatic group, with one, two or three carbon atoms as points of attachment so long as when only one carbon is the point of attachment it is also attached to the double bond, a linear or branched, cyclo, cyclic or acyclic structure, at least one nonaromatic carbon-carbon double bond, no carbon-carbon triple bonds, and no atoms other than carbon and hydrogen. It is noted that while the alkenediyl group is aliphatic, once connected at both ends, this group is not precluded from forming part of an aromatic structure. The terms "alkene" or "olefin" are synonymous and refer to a compound having the formula H—R, wherein R is alkenyl as this term is defined above. A "terminal alkene" refers to an alkene having just one carbon-carbon double bond, wherein that bond forms a vinyl group at one end of the molecule. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups, —CH=CHF, —CH=CHCl and —CH=CHBr, are non-limiting examples of substituted alkenyl groups.

The term "alkynyl" when used without the "substituted" modifier refers to an monovalent unsaturated aliphatic group with a carbon atom as the point of attachment, a linear or branched, cyclo, cyclic or acyclic structure, at least one carbon-carbon triple bond, and no atoms other than carbon and hydrogen. As used herein, the term alkynyl does not preclude the presence of one or more non-aromatic carbon-carbon double bonds. The groups, —C≡CH, —C≡CCH$_3$, and —CH$_2$C≡CCH$_3$, are non-limiting examples of alkynyl groups. An "alkyne" refers to the compound HR, wherein R is alkynyl. The term "alkynediyl" when used without the "substituted" modifier refers to a divalent unsaturated aliphatic group, with two saturated or unsaturated carbon atoms as the points of attachment, a linear or branched, cyclo, cyclic or acyclic structure, no carbon-carbon double bonds and at least one non-aromatic carbon-carbon triple bonds, and no atoms other than carbon and hydrogen. The term "alkynetriyl" when used without the "substituted" modifier refers to a trivalent unsaturated aliphatic group, with one, two or three saturated or unsaturated carbon atoms as the points of attachment provided that when one or two carbon atoms are the point of attachment than those carbon atoms are not also attached to the triple bond, a linear or branched, cyclo, cyclic or acyclic structure, no carbon-carbon double bonds and at least one non-aromatic carbon-carbon triple bond, and no atoms other than carbon and hydrogen. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl or aralkyl groups (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and a monovalent group derived from biphenyl. The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl, aryl or aralkyl groups (carbon number limitation permitting) attached to the first aromatic ring or any additional aromatic ring present. If more than one ring is present, the rings may be fused or unfused. Unfused rings may be connected via one or more of the following: a covalent bond, alkanediyl, or alkenediyl groups (carbon number limitation permitting). Non-limiting examples of arenediyl groups include:

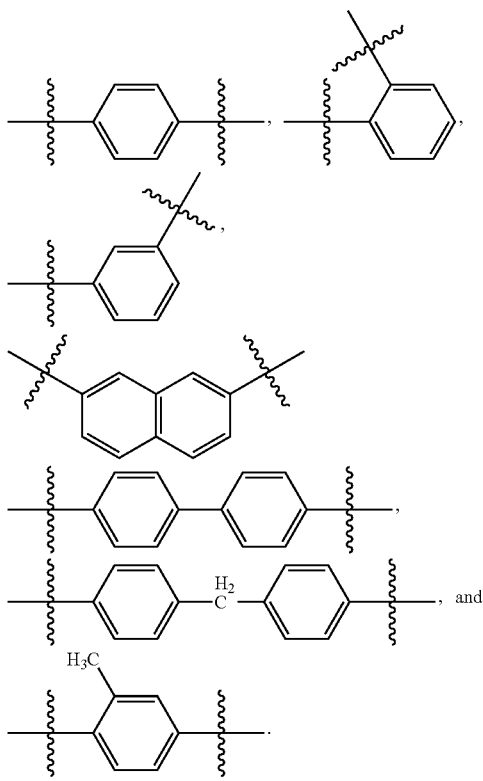

The term "arenetriyl" when used without the "substituted" modifier refers to a trivalent aromatic group with three aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl, aryl or aralkyl groups (carbon number limitation permitting) attached to the first aromatic ring or any additional aromatic ring present. If more than one ring is present, the rings may be fused or unfused. Unfused rings may be connected via one or more of the following: a covalent bond, alkanediyl, or alkenediyl groups (carbon number limitation permitting). An "arene" refers to the compound H—R, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "acyl" when used without the "substituted" modifier refers to the group —C(O)R, in which R is a hydrogen, alkyl, aryl, aralkyl or heteroaryl, as those terms are defined above. The groups, —CHO, —C(O)CH$_3$ (acetyl, Ac), —C(O)CH$_2$CH$_3$, —C(O)CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$CH$_3$, —C(O)CH$_2$C$_6$H$_5$, —C(O)(imidazolyl) are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkane, as defined above, wherein at least one of the hydrogen atoms has been replaced with a —CHO group. When any of these terms are used with the "substituted" modifier one or more hydrogen atom (including a hydrogen atom directly attached the carbonyl or thiocarbonyl group, if any) has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkoxy" when used without the "substituted" modifier refers to the group —OR, in which R is an alkyl, as that term is defined above. Non-limiting examples of alkoxy groups include: —OCH$_3$ (methoxy), —OCH$_2$CH$_3$ (ethoxy), —OCH$_2$CH$_2$CH$_3$, —OCH(CH$_3$)$_2$ (isopropoxy), —O(CH$_3$)$_3$ (tert-butoxy), —OCH(CH$_2$)$_2$, —O-cyclopentyl, and —O-cyclohexyl. The terms "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is alkenyl, alkynyl, aryl, aralkyl, heteroaryl, heterocycloalkyl, and acyl, respectively. The term "alkoxydiyl" refers to the divalent group —O-alkanediyl-, —O-alkanediyl-O—, or -alkanediyl-O-alkanediyl-. The term "alkoxytriyl" refers to the trivalent group —O-alkanetriyl-, —O-alkanetriyl-O—, -alkanetriyl-O-alkanediyl-, or -alkanediyl-O-alkanetriyl-. The term "alkylthio" and "acylthio" when used without the "substituted" modifier refers to the group —SR, in which R is an alkyl and acyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "alkylamino" when used without the "substituted" modifier refers to the group —NHR, in which R is an alkyl, as that term is defined above. Non-limiting examples of alkylamino groups include: —NHCH$_3$ and —NHCH$_2$CH$_3$. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH$_3$)$_2$, —N(CH$_3$)(CH$_2$CH$_3$), and N-pyrrolidinyl. The terms "alkoxyamino", "alkenylamino", "alkynylamino", "arylamino", "aralkylamino", "heteroarylamino", "heterocycloalkylamino" and "alkylsulfonylamino" when used without the "substituted" modifier, refers to groups, defined as —NHR, in which R is alkoxy, alkenyl, alkynyl, aryl, aralkyl, heteroaryl, heterocycloalkyl, and alkylsulfonyl, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$. The term "alkylimino" when used without the "substituted" modifier refers to the divalent group =NR, in which R is an alkyl, as that term is defined above. The term "alkylaminodiyl" refers to the divalent group —NH-alkanediyl-, —NH-alkanediyl-NH, or -alkanediyl-NH-alkanediyl-. The term "alkylaminotriyl" refers to the trivalent group —N(-alkanediyl-)$_2$, —NH-alkanetriyl-NH—, -alkanetriyl-NH-alkanediyl- or -alkanediyl-NH-alkanetriyl-. When any of these terms is used with the "substituted" modifier one or more hydrogen atom have been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups —NHC(O)OCH$_3$ and —NHC(O)NHCH$_3$ are non-limiting examples of substituted amido groups.

The term "boronic acid" when used in the context of this application refers to the group —B(OH)$_2$ or its hydrated analog —B(OH)$_3$$^-$. The term "boronic ester" when used without the "substituted" modifier refers to the group —B(OR)(OR') or its analog —B(OR)(OR')(OR")$^-$ in which R and R' are an alkyl, as that term is defined above, or are taken together as an alkanediyl, as that term is defined above, and R" is either hydrogen or alkyl. A non-limiting example of a "boronic ester" is —B(OMe)$_2$. When the term "boronic ester" is used with the "substituted" modifier one or more hydrogen atoms has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups —B(OCH$_2$CH$_2$NH$_2$)(OMe) and —B(OH)(OCH$_2$Br) are non-limiting examples of substituted boronic esters.

The term "alkylurea" when used in the context of this application refers to the group —NRC(=O)NR'R" in which one, two, or all of R, R', and R" are an alkyl, as that term is defined above, or R and R', R and R", or R' and R" are taken together as alkanediyl, as that term is defined above while any one of R, R', and R" that are not alkyl are hydrogen. Specifically, the term "dialkylurea" and "trialkylurea" may be used to refer to a compound in which two of R, R', and R" and all three of R, R', and R" are alkyl, respectively. While the terms "dialkylurea" and "trialkylurea" can be used they are also encompassed by the general term "alkylurea". Some non-limiting examples of an "alkylurea" include —N(CH$_3$)C(=O)NH$_2$, —N(CH$_2$CH$_3$)C(=O)N(CH$_3$)$_2$, or —NHC(=O)N(CH$_2$CH$_3$)(CH$_3$). When any of these terms are used with the "substituted" modifier one or more hydrogen atoms have been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. Non-limiting examples of substituted alkylurea include —N(CF$_3$)C(=O)N(CF$_3$)$_2$ or —NHC(=O)N(CH$_2$OH)(CH$_2$CO$_2$H).

The term "alkylguanidinyl" when used in the context of this application refers to the group —NRC(=NR")NR'R''' in which one, two, three, or all of R, R', R", and R''' are an alkyl, as that term is defined above, or R and R', R and R", R and R''', R' and R", R' and R''', or R" and R''' are taken together as alkanediyl, as that term is defined above while any one of R, R', R", and R''' that are not alkyl are hydrogen. Specifically, the term "dialkylguanidinyl", "trialkylguanidinyl", and "tetraalkylguanidinyl" may be used to refer to a compound in which two of R, R', R", and R''', three of R, R', R", and R''', and all four of R, R', R", and R''' are alkyl, respectively. While the terms "dialkylguanidinyl", "trialkylguanidinyl", and "tetraalkylguanidinyl" can be used to specifically note they are also encompassed by the general term "alkylguanidinyl". Some non-limiting examples of an "alkylguanidinyl" include —N(CH$_3$)C(=NH)NH$_2$, —N(CH$_2$CH$_3$)C(=NH)N(CH$_3$)$_2$, —N(CH$_2$CH$_3$)C(=N(CH$_3$))N(CH$_3$)$_2$, or —NHC(=N(CH$_3$))N(CH$_2$CH$_3$)(CH$_3$). When any of these terms are used with the "substituted" modifier one or more hydrogen atoms have been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. Non-limiting examples of substituted alkylurea include —N(CF$_3$)C(=NH)N(CF$_3$)$_2$ or —NHC(=NH)N(CH$_2$OH)(CH$_2$CO$_2$H).

The terms "alkylsulfonyl" and "alkylsulfinyl" when used without the "substituted" modifier refers to the groups —S(O)$_2$R and —S(O)R, respectively, in which R is an alkyl, as that term is defined above. The terms "alkenylsulfonyl", "alkynylsulfonyl", "arylsulfonyl", "aralkylsulfonyl", "heteroarylsulfonyl", and "heterocycloalkylsulfonyl" are defined in an analogous manner. When any of these terms is used with the "substituted" modifier one or more hydrogen atoms have been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "alkylphosphate" when used without the "substituted" modifier refers to the group —OP(O)(OH)(OR), in which R is an alkyl, as that term is defined above. Non-limiting examples of alkylphosphate groups include: —OP(O)(OH)(OMe) and —OP(O)(OH)(OEt). The term "dialkylphosphate" when used without the "substituted" modifier refers to the group —OP(O)(OR)(OR')—, in which R and R' can be the same or different alkyl groups, or R and R' can be taken together to represent an alkanediyl. Non-limiting examples of dialkylphosphate groups include: —OP(O)(OMe)$_2$, —OP(O)(OEt)(OMe) and —OP(O)(OEt)$_2$. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)

$CH_3$, —$NHCH_3$, —$NHCH_2CH_3$, —$N(CH_3)_2$, —$C(O)NH_2$, —$OC(O)CH_3$, or —$S(O)_2NH_2$.

The term "alkylphosphoamino" when used without the "substituted" modifier refers to the group —NRP(O)(OH)(OH) or —OP(O)(OH)(NRR')—, in which R and R' can be the same or different alkyl groups, or R and R' can be taken together to represent an alkanediyl, as those terms is defined above. Non-limiting examples of alkylphosphoamino groups include: —NMeP(O)(OH)(OH) and —OP(O)(OH)(NMe$_2$). The term "dialkylphosphoamino" when used without the "substituted" modifier refers to the group —NRP(O)(OR')(OR") or —OP(O)(OR)(NR'R"), in which R, R', and R" can be the same or different alkyl groups, or R and R' or R' and R" can be taken together to represent an alkanediyl. Non-limiting examples of dialkylphosphoamino groups include: —OP(O)(OMe)(NHMe), —NMeP(O)(OH)(OMe) and —OP(O)(NMe$_2$). When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. The chiral centers of the macromolecules of the present disclosure can have the S- or the R-configuration, as defined by the IUPAC 1974 Recommendations. As used herein, the phrase "substantially free from other stereoisomers" means that the composition contains ≤15%, more preferably ≤10%, even more preferably ≤5%, or most preferably ≤1% of another stereoisomer(s).

The above definitions supersede any conflicting definition in any of the reference that is incorporated by reference herein. The fact that certain terms are defined, however, should not be considered as indicative that any term that is undefined is indefinite. Rather, all terms used are believed to describe the disclosure in terms such that one of ordinary skill can appreciate the scope and practice the present disclosure.

D. PHARMACEUTICAL PREPARATIONS

Certain of the methods set forth herein pertain to methods involving the administration of a pharmaceutically and/or therapeutically effective amount of a compound of the present disclosure for purposes of treating a deficiency in red blood cells or to increase the recovery of hematopoietic stem cells.

Moreover, it will be generally understood that a compound of the present disclosure can be provided in prodrug form, also discussed above, meaning that an environment to which a compound of the present disclosure is exposed alters the prodrug into an active, or more active, form. For example, one or more carboxylates on the compounds can be covered into esters which are cleaved in vivo to produce the active compound. It is contemplated that the term "precursor" covers compounds that are considered "prodrugs."

1. Pharmaceutical Formulations and Routes for Administration to Subjects

Any compound discussed herein is contemplated as comprised in a pharmaceutical composition. Pharmaceutical compositions of the present disclosure comprise an effective amount of one or more candidate substances (e.g., a compound of the present disclosure) or additional agents dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains at least one candidate substance or additional active ingredient will be known to those of skill in the art in light of the present disclosure, as exemplified by Remington's Pharmaceutical Sciences, 18$^{th}$ Ed. Mack Printing Company, 1990, incorporated herein by reference. Moreover, for animal (e.g., human) administration, it will be understood that preparations should meet sterility, pyrogenicity, general safety and purity standards as required by the FDA's Center of Drug Evaluation and Research.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, pp 1289-1329, 1990). Except insofar as any conventional carrier is incompatible with the active ingredient, its use in the therapeutic or pharmaceutical compositions is contemplated.

The candidate substance may comprise different types of carriers depending on whether it is to be administered in solid, liquid or aerosol form, and whether it needs to be sterile for such routes of administration as injection. The present disclosure can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intramuscularly, subcutaneously, subconjunctival, intravesicularlly, mucosally, buccally, transdermally, intrapericardially, intraumbilically, intraocularally, orally, locally, via inhalation (e.g., aerosol inhalation), via injection, via infusion, via continuous infusion, via localized perfusion bathing target cells directly, via a catheter, via eye or ear drops, via a lavage, in cremes, in lipid compositions (e.g., liposomes), or by other method or any combination of the foregoing as would be known to one of ordinary skill in the art (see, for example, Remington's Pharmaceutical Sciences, 1990).

A composition comprising a compound of the present disclosure may be formulated for topical administration, for example, in a cream as mentioned, or in an ointment, salve, spray, gel, lotion, or emulsion. The composition may be formulated for transmucosal, transepithelial, transendothelial, or transdermal administration. One example of transdermal formulation is a patch. The composition may further comprise a chemical penetration enhancer, a membrane permeability agent, a membrane transport agent, a preservative, a surfactant, or a stabilizer, as these terms are known to those of skill in the art.

In one topical embodiment, the present disclosure can utilize a patch. A transdermal or "skin" patch is a medicated adhesive patch that is placed on the skin to deliver a time released dose of medication through the skin and into the bloodstream. A wide variety of pharmaceuticals can be delivered by transdermal patches. The first commercially available prescription patch was approved by the U.S. Food and Drug Administration in December 1979, which administered scopolamine for motion sickness.

The main components to a transdermal patch are (a) a liner to protect the patch during storage (removed prior to use); (b) the active agent; (c) an adhesive that serves to adhere the components of the patch together along with adhering the patch to the skin; (d) a membrane to control the release of the drug from the reservoir and multi-layer patches; and (e) a backing that protects the patch from the outer environment.

There are four main types of transdermal patches. Single-layer Drug-in-Adhesive patches have an adhesive layer that also contains the agent. In this type of patch the adhesive layer not only serves to adhere the various layers together, along with the entire system to the skin, but is also responsible for the releasing of the drug. The adhesive layer is surrounded by a temporary liner and a backing. Multi-layer Drug-in-Adhesive patches are similar to the single-layer system in that both adhesive layers are also responsible for the releasing of the drug. The multi-layer system is different however that it adds another layer of drug-in-adhesive, usually separated by a membrane (but not in all cases). This patch also has a temporary liner-layer and a permanent backing. Reservoir patches are unlike the Single-layer and Multi-layer Drug-in-Adhesive systems in that the reservoir transdermal system has a separate drug layer. The drug layer is a liquid compartment containing a drug solution or suspension separated by the adhesive layer. This patch is also backed by the backing layer. In this type of system the rate of release is zero order. Matrix patches have a drug layer of a semisolid matrix containing a drug solution or suspension. The adhesive layer in this patch surrounds the drug layer partially overlaying it.

In another form of treatment, a topical application of a compound of the present disclosure is targeted at a natural body cavity such as the mouth, pharynx, esophagus, larynx, trachea, pleural cavity, peritoneal cavity, or hollow organ cavities including the bladder, colon or other visceral organs. A variety of methods may be employed to affect the topical application into these visceral organs or cavity surfaces. For example, the pharynx may be affected by simply oral swishing and gargling with solutions comprising a compound of the present disclosure.

In particular embodiments, the composition is administered to a subject using a drug delivery device. Any drug delivery device is contemplated for use in delivering a pharmaceutically effective amount of a compound of the present disclosure.

The actual dosage amount of a composition of the present disclosure administered to an animal patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

The dose can be repeated as needed as determined by those of ordinary skill in the art. Thus, in some embodiments of the methods set forth herein, a single dose is contemplated. In other embodiments, two or more doses are contemplated. Where more than one dose is administered to a subject, the time interval between doses can be any time interval as determined by those of ordinary skill in the art. For example, the time interval between doses may be about 1 hour to about 2 hours, about 2 hours to about 6 hours, about 6 hours to about 10 hours, about 10 hours to about 24 hours, about 1 day to about 2 days, about 1 week to about 2 weeks, or longer, or any time interval derivable within any of these recited ranges.

In certain embodiments, it may be desirable to provide a continuous supply of a pharmaceutical composition to the patient. This could be accomplished by catheterization, followed by continuous administration of the therapeutic agent. The administration could be intra-operative or post-operative.

In certain embodiments, pharmaceutical compositions may comprise, for example, at least about 0.1% of a compound of the present disclosure. In other embodiments, a compound of the present disclosure may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg body weight, about 50 microgram/kg body weight, about 100 microgram/kg body weight, about 200 microgram/kg body weight, about 350 microgram/kg body weight, about 500 microgram/kg body weight, about 1 milligram/kg/body weight, about 5 milligram/kg body weight, about 10 milligram/kg/body weight, about 20 milligram/kg body weight, about 50 milligram/kg body weight, about 100 milligram/kg body weight, about 200 milligram/kg body weight, about 350 milligram/kg body weight, about 500 milligram/kg body weight, to about 1000 mg/kg body weight or more per administration, and any range derivable therein. In non-limiting examples of a derivable range from the numbers listed herein, a range of about 5 mg/kg body weight to about 100 mg/kg body weight, about 5 microgram/kg/body weight to about 500 milligram/kg body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal, or combinations thereof.

The candidate substance may be formulated into a composition in a free base, neutral, or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, glycolic, lactic, tartaric, or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine, TRIS, or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. It may be preferable to include isotonic agents, such as, for example, sugars, sodium chloride, or combinations thereof.

In other embodiments, one may use eye or ear drops, nasal solutions or sprays, aerosols or inhalants in the present disclosure. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in certain embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments the candidate substance is prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. In certain embodiments, carriers for oral administration comprise inert diluents, assimilable edible carriers or combinations thereof. In other aspects of the disclosure, the oral composition may be prepared as a syrup or elixir. A syrup or elixir, and may comprise, for example, at least one active agent, a sweetening agent, a preservative, a flavoring agent, a dye, a preservative, or combinations thereof.

Dosage formulations of the present pharmaceutical compositions can be prepared by combining them with a pharmaceutically acceptable carrier, such as a slow release agent, to make either immediate or slow release formulations as is well known in the art. Such compositions could be used, for example, in the treatment of periodontal disease and other oral care indications. Such pharmaceutically acceptable carriers may be either solid or liquid in form such as, for example, cornstarch, lactose, sucrose, peanut oil, olive oil, sesame oil, propylene glycol and water. If a solid carrier is used, the dosage formulation of the present pharmaceutical compositions may be in, for example, powder, troche, or lozenges form. If a liquid carrier is used, the dosage formulation of the present pharmaceutical compositions may be in, for example, soft gelatin capsule, syrup liquid suspension, emulsion, or solution form. The dosage formulations may also contain adjuvants, such as preserving, stabilizing, wetting or emulsifying agents, or solution promoters Immediate and slow release formulations are well known in the art and have been described, for example, in U.S. Pat. No. 4,764,377 (the disclosure of which is incorporated herein by reference), which describes a method for treating periodontal disease by means of a delivery device placed within the periodontal pocket so that release of a therapeutic agent occurs in the immediate vicinity of the disease process. Other means of treating periodontal disease are described in U.S. Pat. No. 5,324,756, the entire contents of which are incorporated herein by reference.

In certain embodiments an oral composition may comprise one or more binders, excipients, disintegration agents, lubricants, flavoring agents, or combinations thereof. In certain embodiments, a composition may comprise one or more of the following: a binder, such as, for example, gum tragacanth, acacia, cornstarch, gelatin or combinations thereof an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar, or both.

Certain coating materials are those which dissolve at about or at least about a pH of 5 or above, such as at about pH 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0 or above, such as pH of about 6.5 or above. Such coatings therefore only begin to dissolve when they have left the stomach and entered the small intestine. Accordingly, these coatings may be considered enteric coatings. A thick layer of coating is provided which will dissolve in minutes to hours, thereby allowing the capsule underneath to breakup only when it has reached the terminal ileum or the colon. Such a coating can be made from a variety of polymers such as cellulose acetate trimellitate (CAT), hydroxypropylmethyl cellulose phthalate (HPMCP), polyvinyl acetate phthalate (PVAP), cellulose acetate phthalate (CAP) and shellac as described by Healy, 1989. For coatings of cellulose esters, a thickness of 200-250 μm would be suitable.

Non-limiting exemplary coating materials are methyl methacrylates or copolymers of methacrylic acid and methyl methacrylate. Such materials are available as EUDRAGIT™ polymers (Rohm Pharma, Darmstadt, Germany). Eudragits are copolymers of methacrylic acid and methyl methacrylate. Compositions may be based on EUDRAGIT™ L100 and Eudragit S100. EUDRAGIT™

L100 dissolves at pH 6 and upwards and comprises 48.3% methacrylic acid units per g dry substance; EUDRAGIT™ S100 dissolves at pH 7 and upwards and comprises 29.2% methacrylic acid units per g dry substance. Certain coating compositions are based on EUDRAGIT™ L100 and EUDRAGIT™ S100 in the range 100 parts L100:0 parts S100 to 20 parts L100:80 parts S100. A non-limiting exemplary range is 70 parts L100:30 parts S100 to 80 parts L100:20 parts S100. For formulations where the ratio of EUDRAGIT™ L100:S100 is high, a coat thickness of the order 150-200 µm is preferable. This is equivalent to 70-110 mg of coating for a size 0 capsule. For coatings where the ratio EUDRAGIT™ L100:S100 is low, a coat thickness of the order 80-120 µm is preferable, equivalent to 30 to 60 mg coating for a size 0 capsule.

It is specifically contemplated that compounds of the present disclosure may be incorporated into the polymers that act as carriers that are nonabsorbable. Compounds of the present disclosure may be, for example, covalently bonded to such polymers. Such polymers may be, for example, the polymers mentioned above and/or the polymer tails and polymer backbones discussed herein.

Additional formulations which are suitable for other modes of administration include suppositories. Suppositories are solid dosage forms of various weights and shapes, usually medicated, for insertion into the rectum, vagina, or urethra. After insertion, suppositories soften, melt or dissolve in the cavity fluids. In general, for suppositories, traditional carriers may include, for example, polyalkylene glycols, triglycerides, or combinations thereof. In certain embodiments, suppositories may be formed from mixtures containing, for example, the active ingredient in the range of about 0.5% to about 10%, and preferably about 1% to about 2%.

Sterile injectable solutions are prepared by incorporating the active compounds in the required amount in the appropriate solvent with various other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsions, certain methods of preparation may include vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin, or combinations thereof.

2. Combination Therapy

In order to increase the effectiveness of a compound of the present disclosure, a compound of the present disclosure may be combined with traditional drugs. For example, erthyropoietin or a chemotherapeutic agent may be administered in combination with a compound with the present disclosure. It is contemplated that this type of combination therapy may be used in vitro or in vivo.

For example, a compound of the present disclosure may be provided in a combined amount with an effective amount of a second agent (or more) a modulation of the side effects of the other drug. This process may involve administering the agents at the same time or within a period of time wherein separate administration of the substances produces a desired therapeutic benefit. This may be achieved by contacting the cell, tissue, biofilm, or organism with a single composition or pharmacological formulation that includes two or more agents, or by contacting the cell with two or more distinct compositions or formulations, wherein one composition includes one agent and the other includes another.

The compounds of the present disclosure may precede, be co-current with and/or follow the other agents by intervals ranging from minutes to weeks. In embodiments where the agents are applied separately to a cell, tissue, biofilm, or organism, one would generally ensure that a significant period of time did not expire between the time of each delivery, such that the agents would still be able to exert an advantageously combined effect on the cell, tissue or organism. For example, in such instances, it is contemplated that one may contact the cell, tissue or organism with two, three, four or more modalities substantially simultaneously (i.e., within less than about a minute) as the candidate substance. In other aspects, one or more agents may be administered within of substantially simultaneously, about 1 minute, about 5 minutes, about 10 minutes, about 20 minutes about 30 minutes, about 45 minutes, about 60 minutes, about 2 hours, about 3 hours, about 4 hours, about 5 hours, about 6 hours, about 7 hours about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 22 hours, about 23 hours, about 24 hours, about 25 hours, about 26 hours, about 27 hours, about 28 hours, about 29 hours, about 30 hours, about 31 hours, about 32 hours, about 33 hours, about 34 hours, about 35 hours, about 36 hours, about 37 hours, about 38 hours, about 39 hours, about 40 hours, about 41 hours, about 42 hours, about 43 hours, about 44 hours, about 45 hours, about 46 hours, about 47 hours, about 48 hours, about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 1, about 2, about 3, about 4, about 5, about 6, about 7 or about 8 weeks or more, and any range derivable therein, prior to and/or after administering the candidate substance.

Various combination regimens of the agents may be employed. Non-limiting examples of such combinations are shown below, wherein a compound of the present disclosure is "A" and a second agent, such as but not limited to an chemotherapeutic agent, such as atovaquone, azacitidine, bexarotene, boceprevir, bosentan, bosutinib, brentuximab, vedotin, carbidopa-levodopa, carglumic acid, decitabine, eribulin mesylate, foscarnet, metformin, ofatumumab, pomalidomide, pralatrexate solution, ropivacaine, rosiglitazone, sirolimus, temsirolimus, or valganciclovir; an antiretroviral; a non-steroidal anti-inflammatory drug, a steroid, radiation therapy; or immunotherapy is "B":

A/B/A B/A/B B/B/A A/A/B A/B/B B/A/A A/B/B/B B/A/B/B

B/B/B/A B/B/A/B A/A/B/B A/B/A/B A/B/B/A B/B/A/A

B/A/B/A B/A/A/B A/A/A/B B/A/A/A A/B/A/A A/A/B/A

E. EXAMPLES

The following examples are included to demonstrate certain particular embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1: Identification and Synthesis of Suberoylarginine and Derivatives Thereof Identification of SA.

Figure 1B:
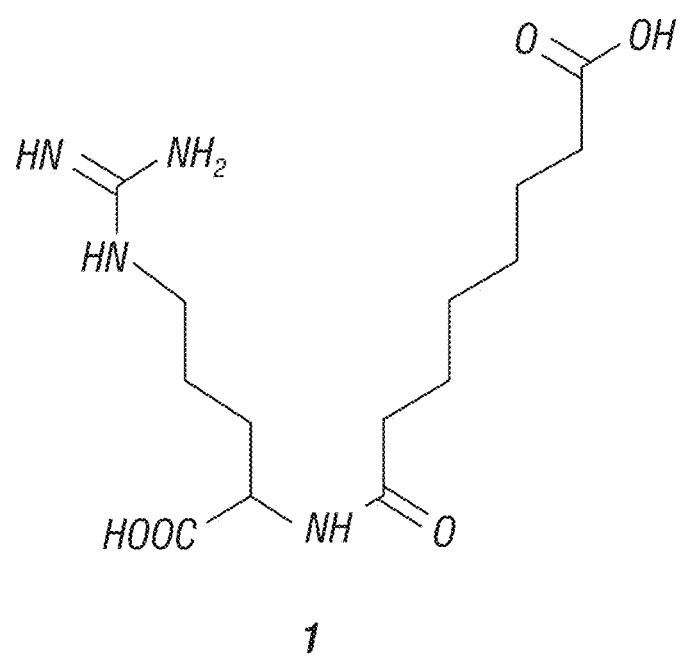
FIG. 1B show the structure of SA.

To isolate the active component from the Chan Su extract, the inventors first removed the toxic lipid-soluble components, for example, the bufotenines, by extracting with chloroform and ethanol (FIG. 1A). The water-soluble extract was then fractionated by preparative HPLC on a C18 column. Over 50 fractions were collected and pooled into 11 major fractions for in vivo studies. These fractions were individually injected into sublethally irradiated mice, and hematopoietic regeneration was monitored. The inventors also monitored ex vivo expansion of HSCs followed by bone marrow transplantation (Zheng et al., 2011; 2012) in animals treated with these fractions. The active major fraction was further fractionated by HPLC into 12 sub-fractions and subjected to functional assays. The high-resolution NMR and mass spectra of the final active fraction suggested that the active component is suberoyl arginine (SA) (FIG. 1B). SA was previously identified as a component of toad venoms as a likely hydrolysis product of bufadienolides (Gao et al., 2010), but its function is not known (Barry et al., 1996; Ye and Guo, 2005; Xu et al., 2007).

Chemically Synthesized SA Promotes Regeneration of Hematopoietic System in Mice.

Figure 2A:
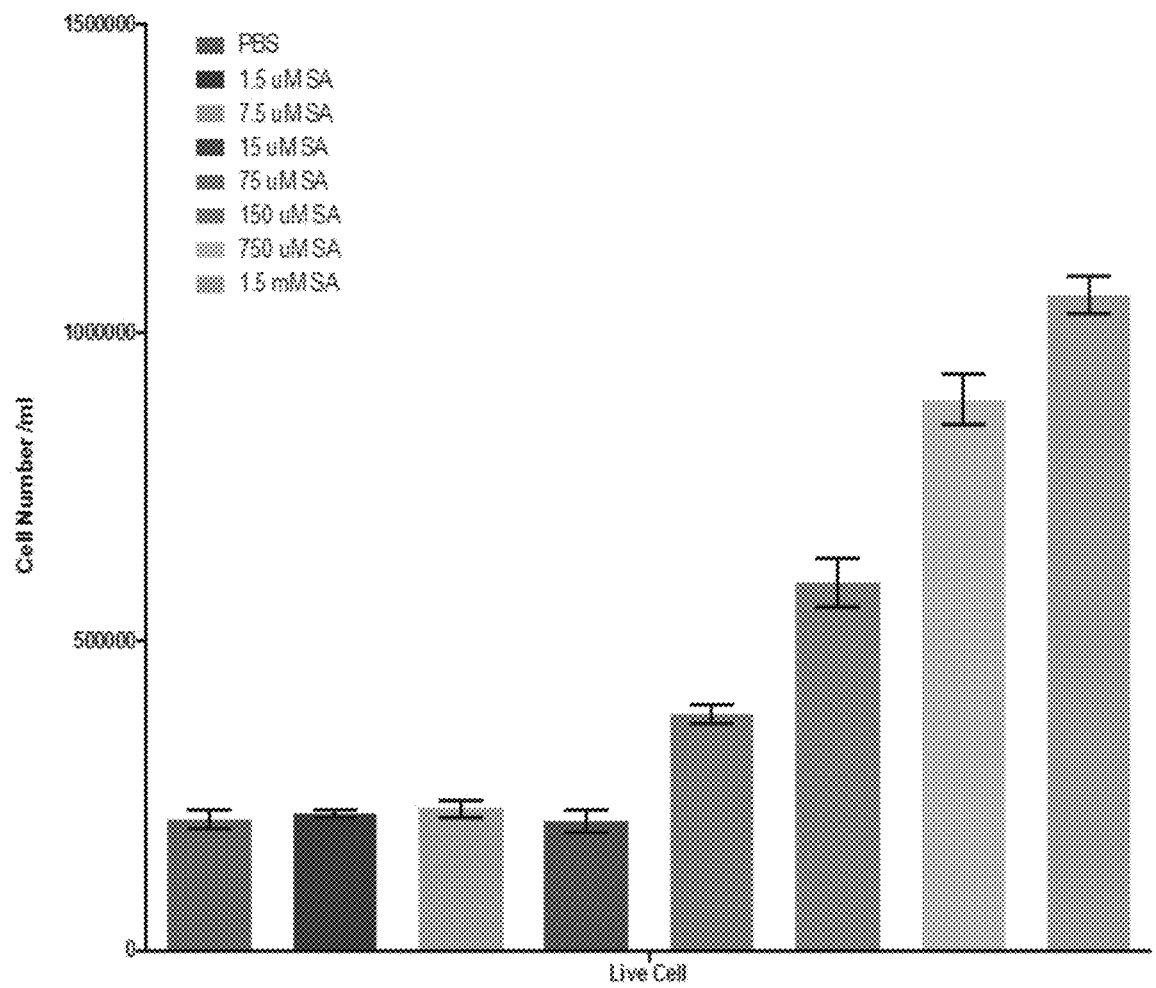
FIG. 2A shows that SA promotes proliferation of mouse HSCs. Mouse BM Lin-Sca-1+Kit+CD34-Flk2-cells were cultured in serum-free Stemspan medium with 10 ng/ml SCF, 20 ng/ml TPO, and indicated concentrations of SA. Cell numbers were counted after 6 days.
Figure 2B:
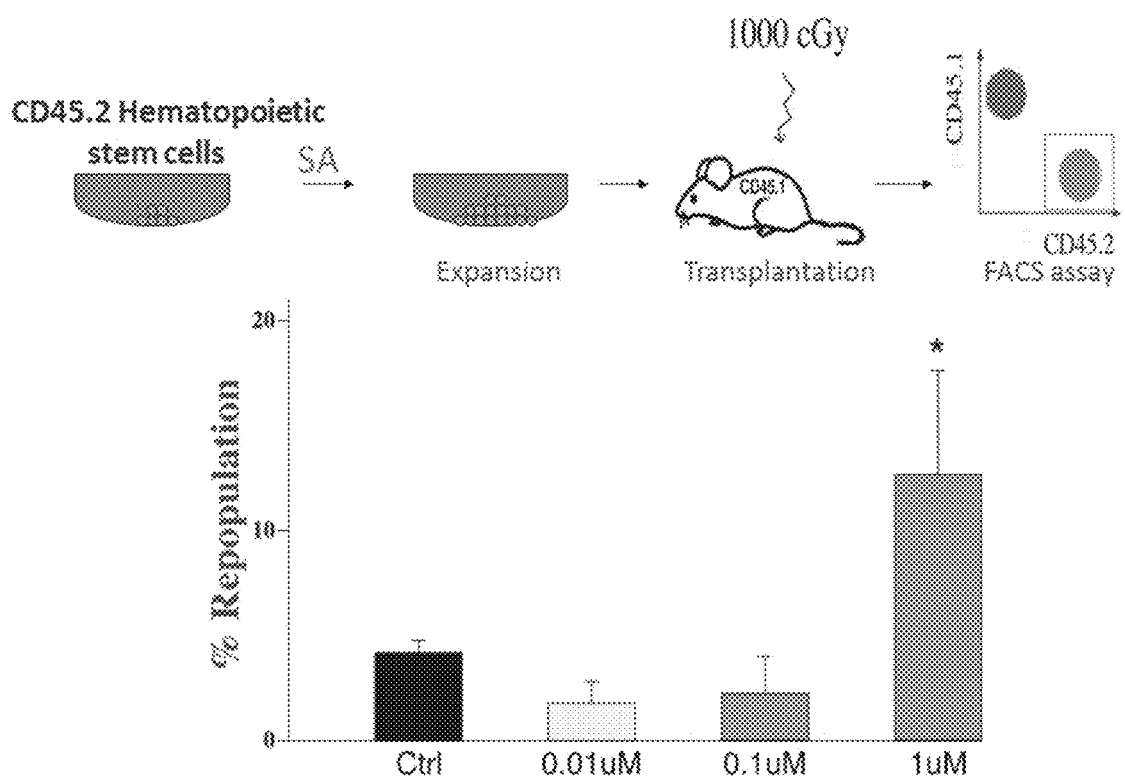
FIG. 2B The effects of SA on the ex vivo expansion of mouse CD45.1 Percent repopulation of C57BL/6 bone marrow HSCs at 0, 10 nM, 100 nM, and 1 µM for 8 days, measured at 3 weeks, 7 weeks, and 16 weeks post-transplantation. The repopulation of donor mouse CD45.1 HSCs was determined by transplantation into lethally irradiated (1000 rad) CD45.2 C57BL/6 mice. Ten thousand CD45.2 total bone marrow cells were co-transplanted as competitors. n=5.
Figure 2C:
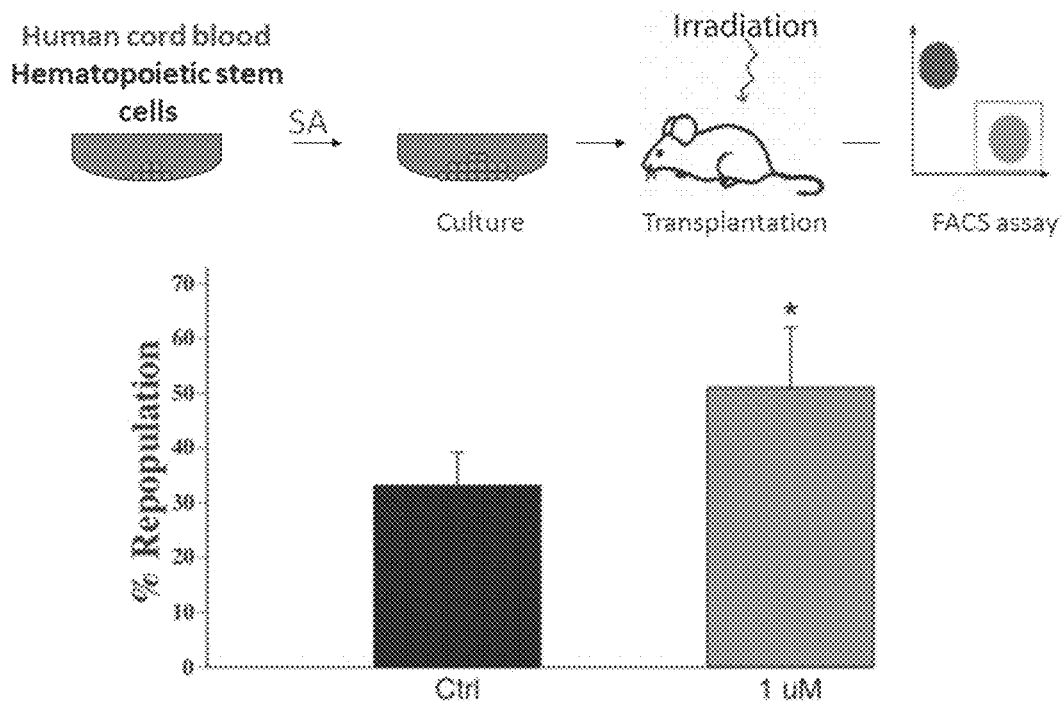
FIG. 2C shows that SA supports ex vivo expansion of 7,000 input equivalent human cord blood HSCs (CD133$^+$ cells) cultured for 11 days at 0 and 1 µM measured at 8 weeks post-transplantation. The repopulation of human hematopoietic stem cells was determined by transplantation into sublethally irradiated (250 rad) NOD/SCID IL2R gamma$^{-/-}$ (NSG) mice. n=7.

To determine whether SA is responsible for the observed hematopoietic effects in mice, the inventors conducted de novo chemical synthesis of SA (Scheme 1). The chemically synthesized SA promoted the proliferation of mouse HSCs (FIG. 2A). Importantly, it also supports the ex vivo expansion of mouse and human HSCs as determined by bone marrow transplantation analyses as the "gold standard" of the measure of HSC activity (FIGS. 2B-C), suggesting that SA has direct effects on HSCs.

Suberoylarginine and its derivatives can be synthesized according to the general reaction scheme described below in Scheme 1. In the scheme, the functional group can be a wide variety of functional groups including amine, guanidine, urea, carboxyl, boronic acid, phosphate, or sulfonic acid when paired with the appropriate protecting groups for that functional group.

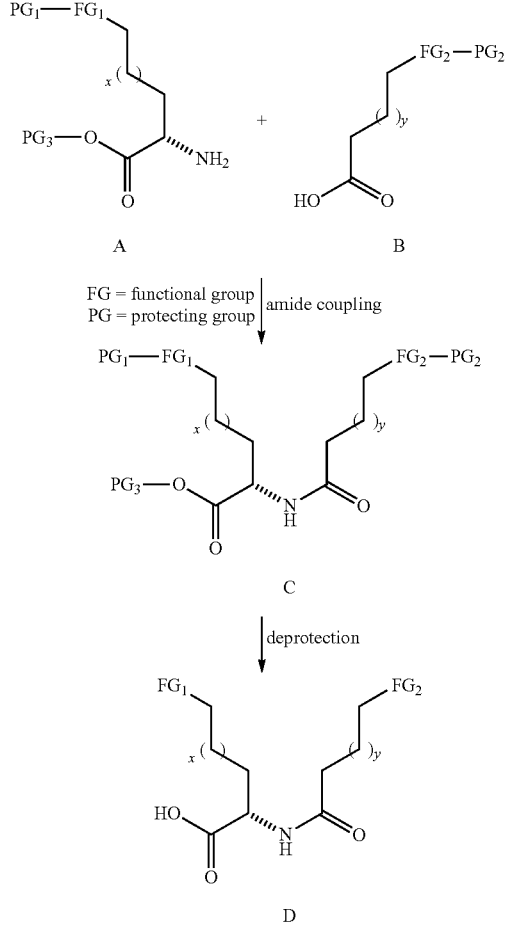

Scheme 1

General Procedure for the Preparation of the Cyclic Carboxylic Anhydrides:

A solution of carboxylic diacid in acetic anhydride (ca. 3 M) was heated at reflux overnight. After cooling to room temperature, acetic anhydride was removed under reduced pressure (ca. 10 mmHg) to give the desired cyclic carboxylic anhydrides.

Suberic Anhydride:

$^1$H NMR (300 MHz, DMSO-d$_6$) δ 2.41 (m, 4H), 1.62 (m, 4H), 1.34 (m, 4H).

General Procedure for the Preparation of the SA Derivatives:

To a solution of amino acid hydrochloride (1 equiv) and sodium bicarbonate (2 equiv) in water (ca. 1 M) was added the carboxylic anhydride (1.1 equiv) at 4° C. slowly. After stirring for 20 min, a few drops of concentrated ammonia-water were added to adjust the pH to 8. The solution was then filtered and washed three times with dichloromethane. The sample was freeze-dried and purified by C18 reverse-phase silica gel chromatography.

Suberoyl Arginine:

$^1$H NMR (500 MHz, D$_2$O) δ 4.19-4.17 (dd, 1H), 3.03 (t, 2H), 2.19 (t, 2H), 2.11 (t, 2H), 1.79-1.71 (m, 1H), 1.62-1.55 (m, 1H), 1.49-1.37 (m, 6H), 1.14-1.12 (m, 4H); $^1$H NMR (500 MHz, DMSO-d$_6$) δ 4.14-4.11 (dd, 1H), 3.09 (t, 2H), 2.17 (t, 2H), 2.10 (t, 2H), 1.71-1.67 (m, 1H), 1.62-1.57 (m, 1H), 1.49 (m, 6H), 1.22 (m, 4H); $^{13}$C NMR (125 MHz, D$_2$O) δ 179.2, 177.3, 175.5, 156.6, 52.3, 40.6, 35.3, 33.8, 27.9, 27.8, 27.7, 25.2, 24.6, 24.3; $^{13}$C NMR (125 MHz, DMSO-$d_6$) δ 175.3, 174.1, 173.5, 157.2, 52.0, 39.3, 35.6, 28.9, 28.5, 25.9, 25.8, 25.0; MS(APCI) calcd for $C_{14}H_{27}N_4O_5$ (M+H)$^+$ 331.2. found 331.1; calcd for $C_{14}H_{25}N_4O_5$ (M−H)$^−$ 329.2. found 329.2.

Example 2: Biological Activity of Suberoylarginine

A. Methods

Ex Vivo Expansion of Mouse Bone Marrow HSCs.

Bone marrow CD45.1 Lin$^−$Sca-1$^+$Kit$^+$Flk2$^−$CD34$^−$ cells were isolated from 8-12 week old CD45.1 C57BL/6 mice and were plated into wells of a U-bottom 96-well plate (3799; Corning). StemSpan serum-free medium (StemCell Technologies) supplemented with 10 μg/mL heparin (Sigma), 10 ng/mL mouse SCF (R&D Systems), 20 ng/mL mouse TPO (R&D Systems), and 10 ng/mL human FGF-1 (Invitrogen), and indicated concentration of suberoylarginine was used. Cells were cultured at 37° C. in 5% $CO_2$ and the normal level of $O_2$ for 8 days. Cells from 12 culture wells were pooled and mixed with CD45.2 total bone marrow competitor cells before transplantation into lethally irradiated (1000 rad) 6-8 week old CD45.2 C57BL/6 recipient mice. For analyzing repopulation of mouse HSCs, peripheral blood cells of recipient mice were collected by retro-orbital bleeding, followed by lysis of red blood cells and staining with anti-CD45.2-FITC, anti-CD45.1-PE, anti-Thy1.2-PE (for T-lymphoid lineage), anti-B220-PE (for B-lymphoid lineage), anti-Mac-1-PE, or anti-Gr-1-PE (cells co-staining with anti-Mac-1 and anti-Gr-1 were deemed to be of the myeloid lineage) monoclonal antibodies (BD Pharmingen). The "percent repopulation" shown in all figures was based on the staining results of anti-CD45.2-FITC and anti-CD45.1-PE. In all cases FACS analysis of the above listed lineages was also performed to confirm multi-lineage reconstitution.

Ex Vivo Expansion of Human Cord Blood HSCs.

Cryopreserved human cord blood CD133$^+$ cells were purchased from AllCells. All of cells were from pooled donors. Purities of CD133$^+$ cells as analyzed by flow cytometry were higher than 90%. After thawing, the cell viability tested by trypan blue exclusion was higher than 72%. The thawed cells were centrifuged and resuspended in StemSpan medium before being aliquoted for immediate transplantation or culture. StemSpan supplemented with 50 ng/mL human SCF, 10 ng/mL human TPO, and 50 ng/mL human Flt3-L was used as culture medium. CD133$^+$ cells were plated at $5 \times 10^3$ cells/well in one well of a U-bottom 96-well plate (3799; Corning) with 200 μl of the indicated medium for 2 days. On day 3, cells were pooled from individual wells and transferred to 6-well plates at $5 \times 10^4$ cells/mL. Fresh medium was added at days 4 and 7 to keep the cell density at $2 \times 10^5$ cells/mL (day 4) or $7 \times 10^5$/mL (day 7). Cells were cultured at 37° C. in 5% $CO_2$ and normal $O_2$ or 5% $O_2$ (low $O_2$) levels. For transplantation, cells from all the culture wells were pooled before the 7000 input equivalent CD133+ cells were injected intravenously via the retro-orbital route into sub-lethally irradiated (250 rad) 8-10 week old NSG mice. Eight weeks after transplantation, bone marrow nucleated cells from transplanted animals were analyzed by flow cytometry for the presence of human cells. Total human hematopoietic cells were determined as CD45/71$^+$, and human myeloid cells as myeloid CD45/71$^+$CD15/66b$^+$.

Mouse Model of Bone Marrow Failure after Chemo- and Radio-Treatment.

Balb/c mice were first treated with 100 mg/kg acetylphenylhydrazine and, after 24 hours, were irradiated with 2 Gy. Two days post radiation treatment, the mice were treated with 62.5 mg/kg cyclophosphamide (CY). This treatment is known to induce sublethal damage to HSCs and RBCs. Two days after the CY treatment, the mice were given daily intraperitoneal injections of SA for 4 to 14 days; a range of SA concentrations was evaluated. Blood counts were measured at days 0, 4, and 8. Additionally, bone marrow Lin$^−$Sca-1$^+$Kit$^+$CD34$^−$Flk2$^−$ (LSKFC) cells that are enriched for HSCs and hematopoietic lineages were quantified at day 14.

Proliferation of Mouse HSCs.

Mouse bone marrow Lin-Sca-1+Kit+CD34-Flk2-cells were cultured in serum-free Stemspan medium with 10 ng/ml SCF, 20 ng/ml TPO, and indicated concentrations of SA. Cell numbers were counted after 6 days.

Stability Test in S9 Extract.

SA (2 mM in $H_2O$ stock, final concentration in mixture is 2 μM) was incubated with Murine S9 (Lot KWB) fraction and Phase I (NADPH Regenerating System) cofactors for 0-240 minutes. Reactions were quenched with 1 mL (1:1) of methanol containing 0.2% formic acid, and 100 ng/ml IS (IS final conc.=10 ng/ml). Samples were vortexed for 15 seconds, incubated at RT for 10 minutes and spun for 5 minutes at 2400 rpm. Supernatant (1 mL) was then transferred to an eppendorf tube and spun in a table top, chilled centrifuge for 5 minutes at 13.2K rpm. Supernatant (800 μl) was transferred to an HPLC vial (w/out insert). Analyzed by Qtrap 3200 mass spectrometer.

Stability Test in Plasma.

1 μl of SA (2 mM DMSO stock) was incubated with 1 ml ACD mouse plasma or saline control to make 2 μM SW125991 working solution. Vortext well and incubate in 37° C. water bath. At time point 0, 10, 30, 60, 120, 240, 1440 min, 100 μl sample was crashed by 200 μl MeOH with IS benzylbenzamide at 15 ng/ml. Centrifuge twice at 13200 rpm for 5 min, and supernatant was injected into LCMS for analysis.

B. Results

Suberoylarginine Effect on Bone Marrow Failure in a Mouse Model.

The inventors tested the effect of SA on HSCs and RBCs in a mouse bone marrow failure model after chemo- and radio-therapy. In this model, Balb/c mice were first treated with 100 mg/kg acetylphenylhydrazine and, after 24 hours, were irradiated with 2 Gy. Two days post radiation treatment, the mice were treated with 62.5 mg/kg cyclophosphamide (CY). This treatment is known to induce sublethal damage to HSCs and RBCs. Two days after the CY treatment, the mice were given daily intraperitoneal injections of SA for 4 to 14 days; a range of SA concentrations was evaluated. Blood counts were measured at days 0, 4, and 8. Additionally, bone marrow Lin$^−$Sca-1$^+$Kit$^+$CD34$^−$Flk2$^−$ (LSKFC) cells that are enriched for HSCs (Christensen and Weissman, 2001) and hematopoietic lineages were quantified at day 14.

Figure 3A:
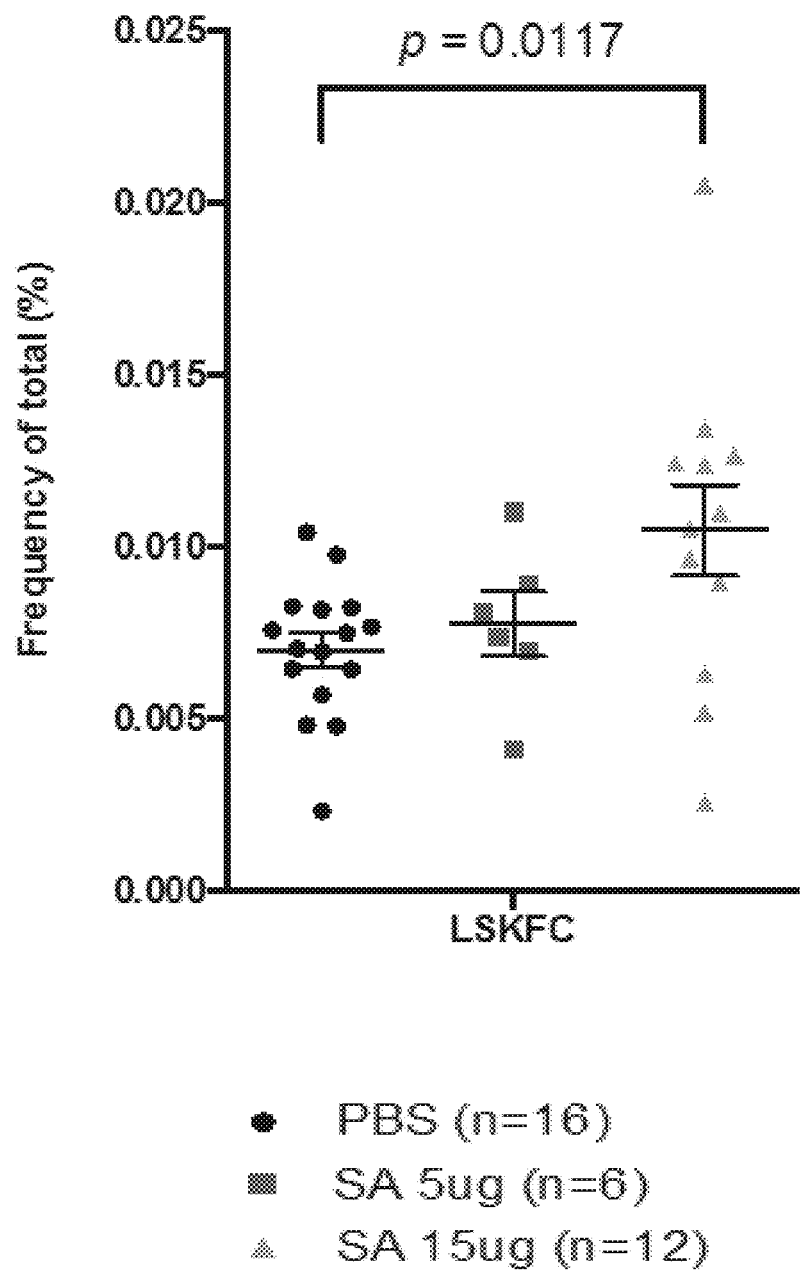
FIGS. 3A-3D show the effects with 5 and 15 µg of subreoylarginine/mouse/day on bone marrow Lin$^-$Sca-1$^+$Kit$^+$CD34$^-$Flk2$^-$ cells (HSCs) (FIG. 3A), red blood cell recovery (FIG. 3B), hematocrit recovery (FIG. 3C), and hemoglobin recovery (FIG. 3D) through 14 days are shown.
Figure 3B:
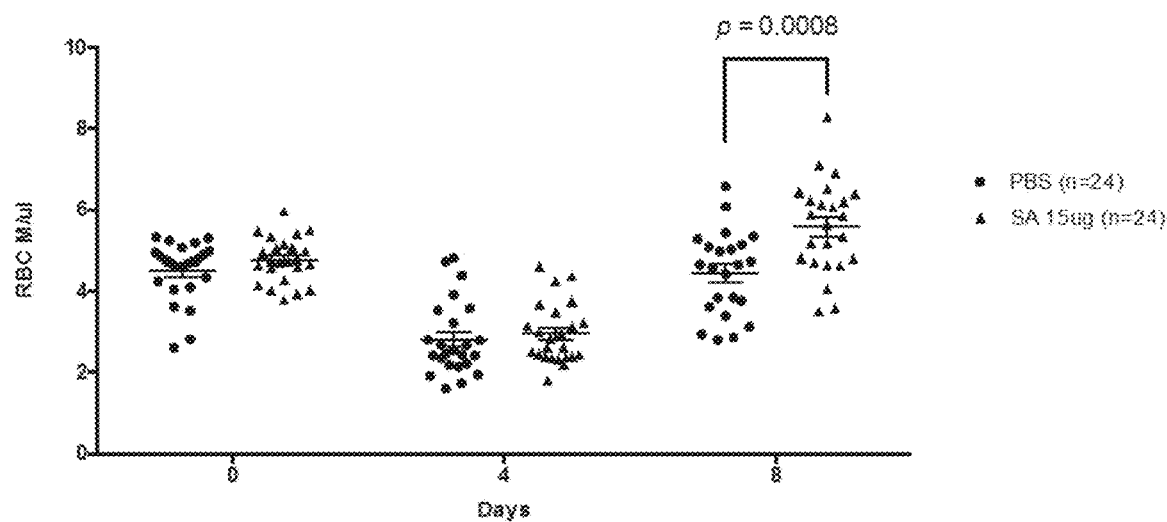
Figure 3C:
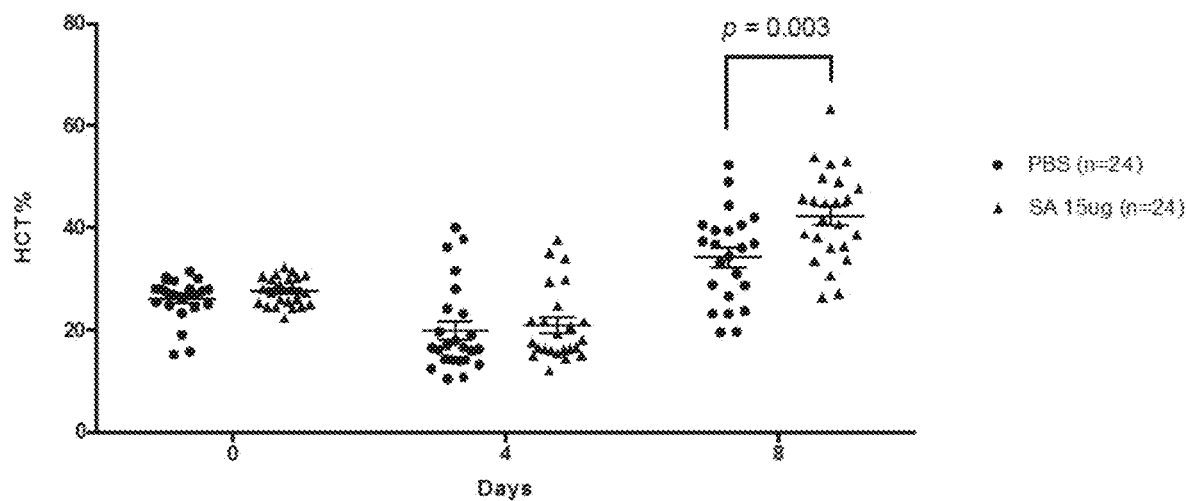
Figure 3D:
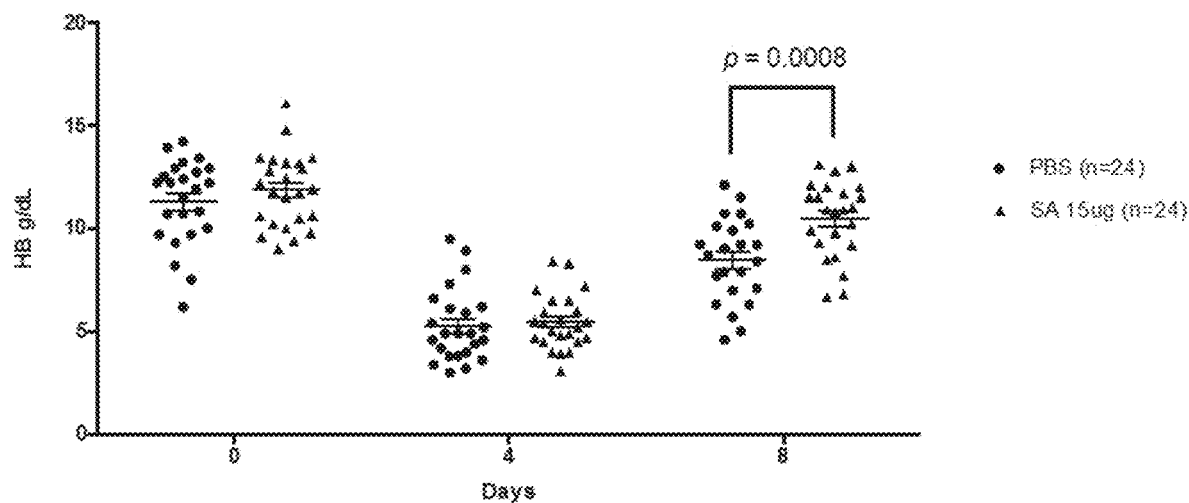
Figure 4:
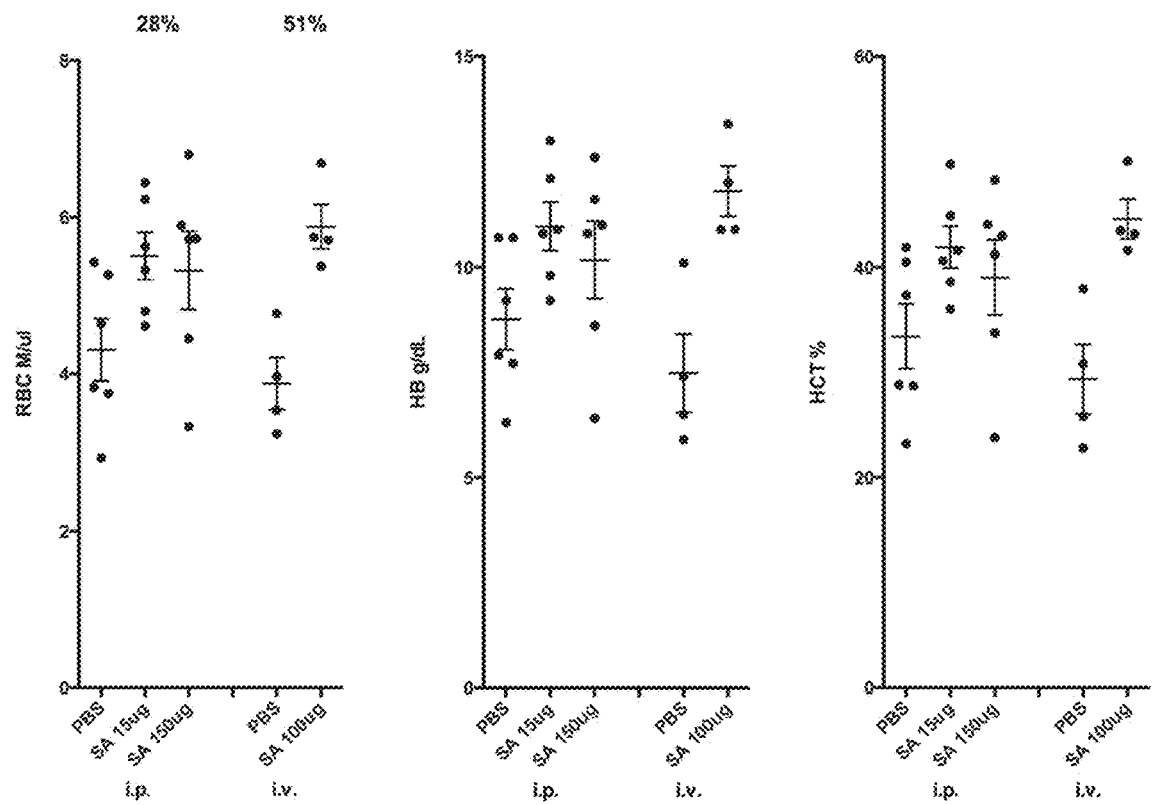
FIG. 4 shows a comparison of SA administration at day 8 following initial treatment with intraperitoneal (ip), oral and intravenous (iv) routes. The % numbers on the top indicate the increases of red blood cells after SA treatment.
Figure 5A:
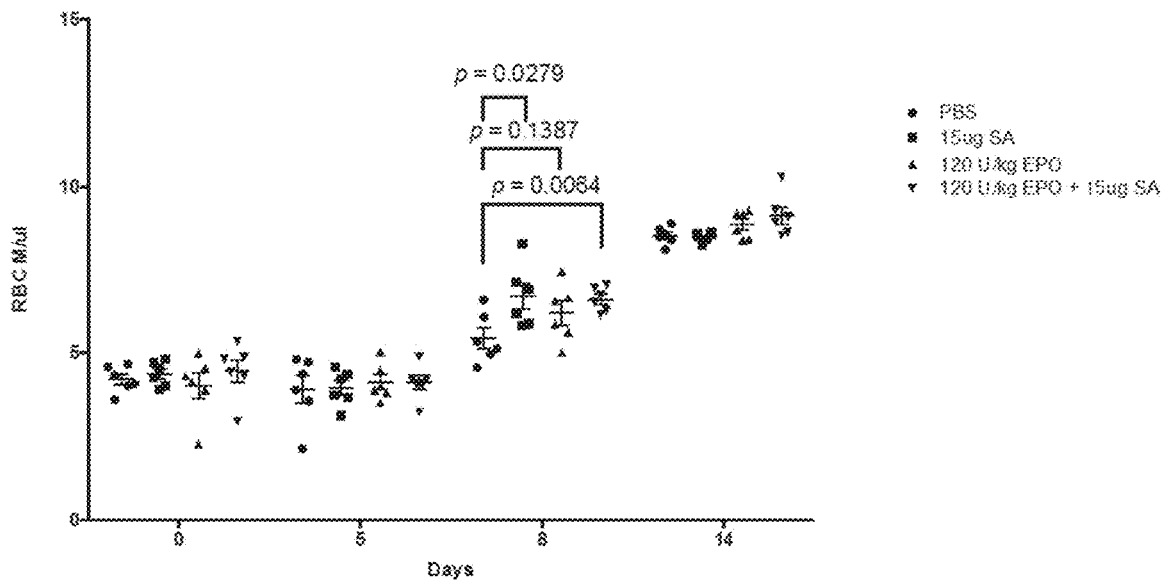
FIGS. 5A-C show various comparisons of the effects of SA (15 µg), EPO (120 U/kg) and SA+EPO (15 g+120 U/kg) in a mouse bone marrow failure model. Red blood cell recovery (FIG. 5A), hematocrit recovery (FIG. 5B), and hemoglobin recovery (FIG. 5C) after 14 days are shown.
Figure 5B:
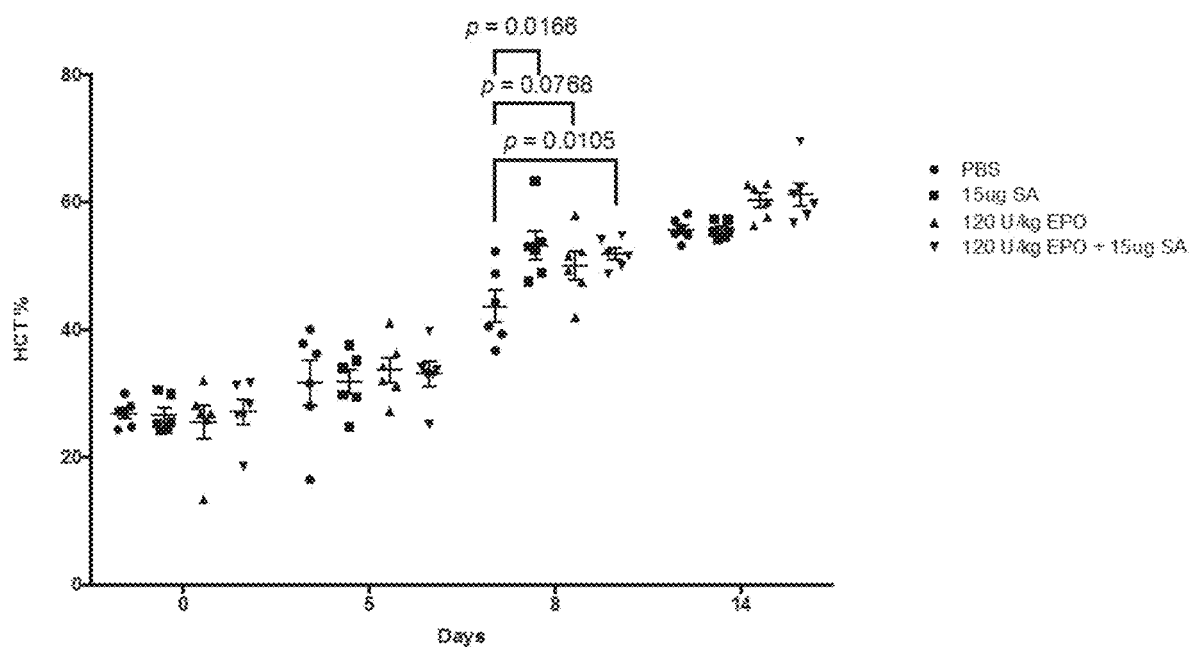
Figure 5C:
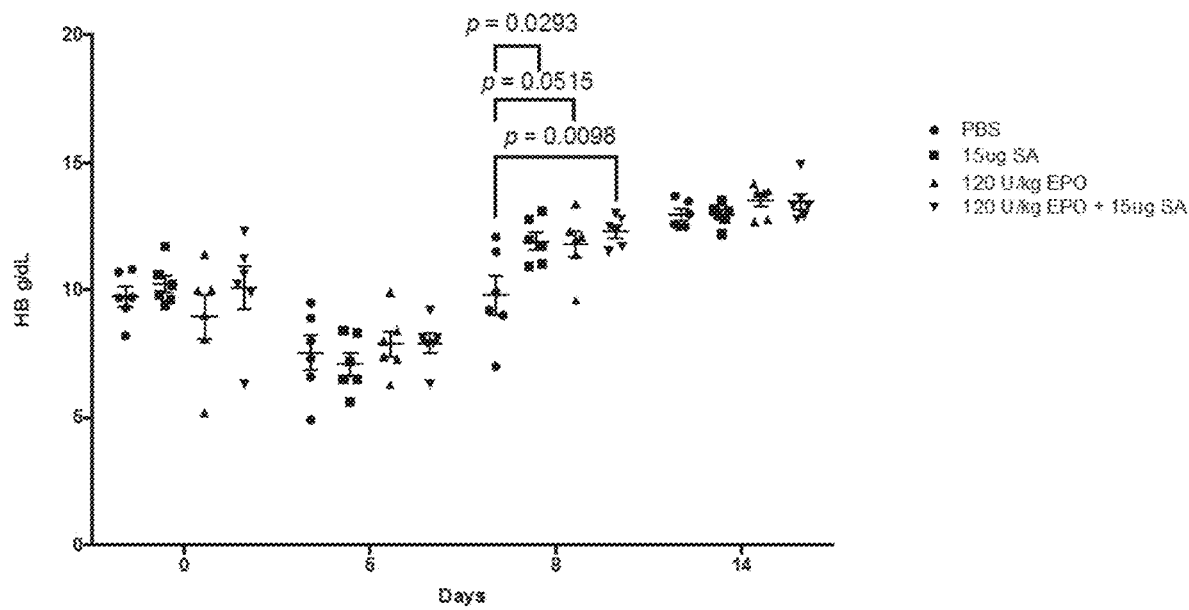

The treatment of 15 μg of SA per mouse (~0.7 mg/kg) intravenously (i.v.) per day for 14 days resulted in ~40% increase of phenotypic bone marrow HSCs (FIG. 3A). SA treatment also significantly increased levels of RBCs, hematocrit, and hemoglobin by 25-30% at day 8 relative to animals not treated with SA (FIGS. 3B-D). Either iv or intraperitoneal (ip) administration of SA works efficiently to stimulate hematopoietic recovery (FIG. 4). Importantly, the effect of SA on RBC recovery was comparable to that of EPO in the same mouse model (FIGS. 5A-C). These data are concordant with reported effects of EPO (20-50% increase of RBC parameters) in mice with phenylhydrazine-induced anemia or chronic kidney disease (Cynshi et al., 1990; Yamaguchi-Yamada et al., 2004). Together, these results strongly suggest that SA is the component in Chan Su that is responsible for its hematopoietic stimulatory effects.

Toxicity and Stability.

Figure 6:
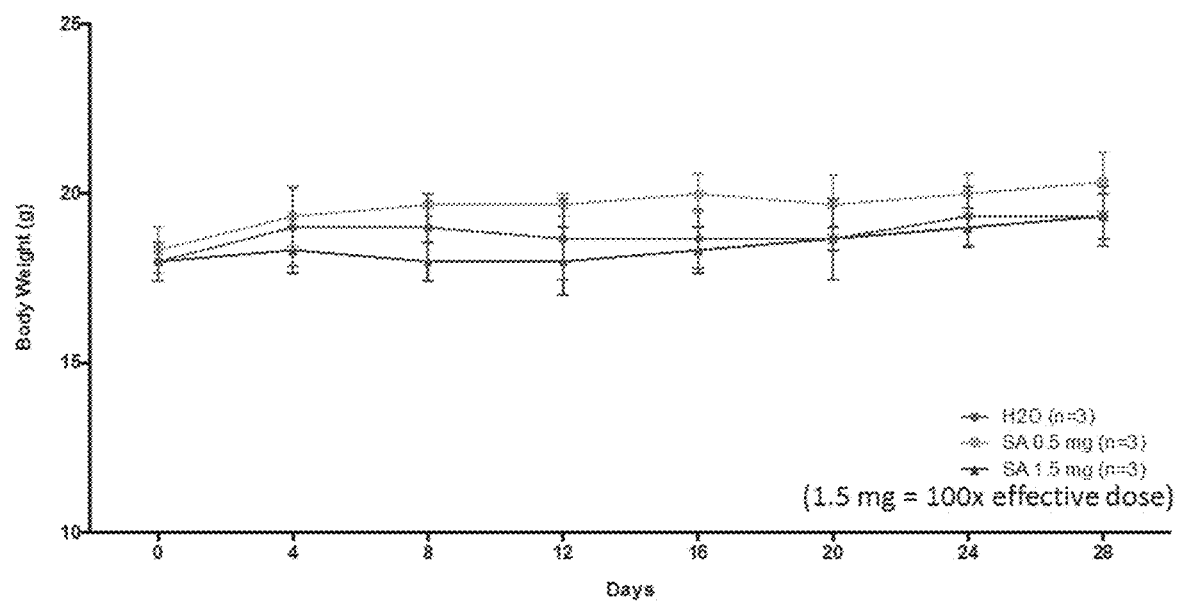
FIG. 6 shows that no detectable toxicity was observed when doses of greater than 33 times and 100 times the effective amount (0.5 mg and 1.5 mg) of subreoylarginine/day were given to mice for 28 days. No significant change of body weight, behavior, or activities of the suberoylarginine treated mice was observed.
Figure 7A:
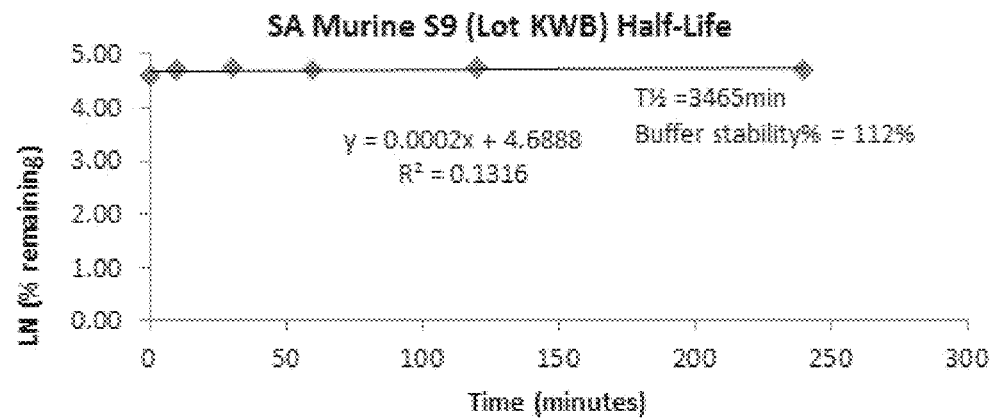
FIGS. 7A-B show that SA is metabolically stable.
Figure 7B:
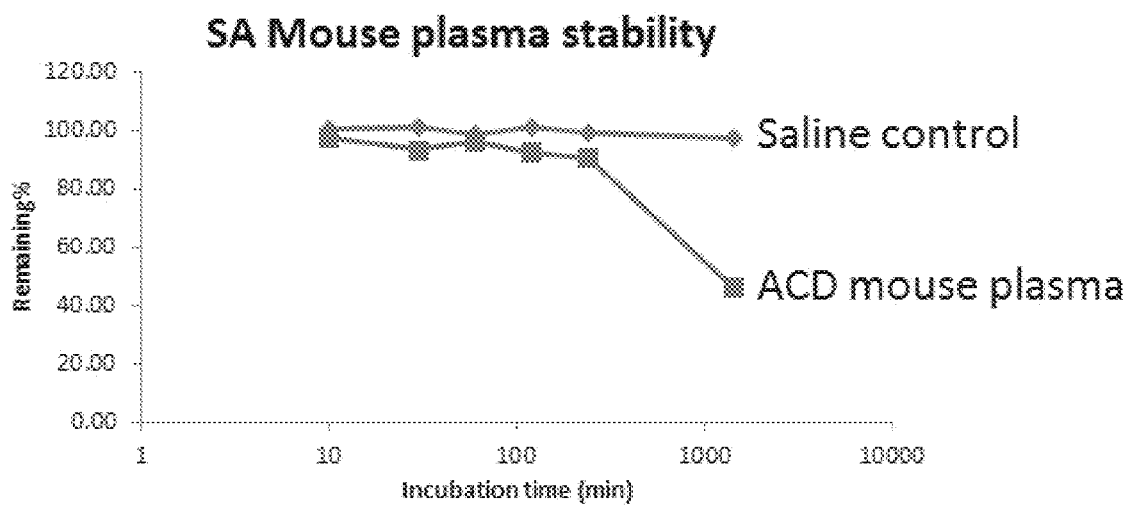

The inventors did not observe any detectable SA toxicity when mice were treated with a dose of 0.5 and 1.5 mg daily for four weeks; this dose is 33- and 100-times the effective amount (FIG. 6). In this experiment, 8-week-old Balb/c mice were given daily injections of SA at doses of 0, 0.5, and 1.5 mg per mouse for 28 days. The body weight and activities of mice were monitored daily. As shown in FIG. 6, SA treatment at these doses did not significantly alter the body weight of mice. In addition, we did not observe any changes in behavior, activity, hematology, serum chemistry, or urinalysis parameters, and no damage was observed to tissues/organs histologically (not shown). Also, SA was metabolically stable in S9 liver fractions and in plasma (FIGS. 7A-B).

All of the methods and apparatuses disclosed and claimed herein can be made and executed without undue experimentation in light of the present disclosure. While the compositions and methods of this disclosure have been described in terms of particular embodiments, it will be apparent to those of skill in the art that variations may be applied to the methods and apparatuses and in the steps or in the sequence of steps of the methods described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

F. REFERENCES

The following references, to the extent that they provide exemplary procedural or other details supplementary to those set forth herein, are specifically incorporated herein by reference.

U.S. Pat. No. 4,764,377
U.S. Pat. No. 5,324,756
Cynshi, et al. "Effects of recombinant human erythropoietin on haemolytic anaemia in mice," *British Journal of Haematology*, 76:414-419, 1990.
Greene and Wuts, "Greene's Protecting Groups in Organic Synthesis," 4$^{th}$ Edition, Wiley-Interscience, 2006.
Liu, et al., "Chan Su extracts as a therapeutic agent for pediatric aplastic anemia: clinical analysis of 25 cases," *J. Human Medical College*, 4:383-386, 1984.
Smith, "*March's Advanced Organic Chemistry: Reactions, Mechanisms, and Structure,*" 7$^{th}$ Edition, Wiley, 2007.
Yamaguchi-Yamada, et al., "Improvement of Anemia Associated with Chronic Renal Failure by Recombinant Human Erythropoietin Treatment in ICR-Derived Glomerulonephritis (ICGN) Mice," *J. Vet. Med. Sci.*, 66(7): 883-886, 2004.
Barry et al., GC/MS comparison of the West Indian aphrodisiac "Love Stone" to the Chinese medication "chan su": bufotenine and related bufadienolides. *J Forensic Sci*, 41:1068-1073, 1996.
Ye and Guo, Analysis of bufadienolides in the Chinese drug ChanSu by high-performance liquid chromatography with atmospheric pressure chemical ionization tandem mass spectrometry. *Rapid Commun Mass Spectrom*, 19:1881-1892, 2005.
Xu et al., Simultaneous determination of five main active bufadienolides of Chan Su in rat plasma by liquid chromatography tandem mass spectrometry. *J Chromatogr B Analyt Technol Biomed Life Sci*, 859:157-163, 2007.
Liu et al., Chan Su extracts used as a therapeutic agent for pediatric aplastic anemia: clinical analyses of 25 cases. *Journal of Hunan Medical College*, 4:383-386, 1984.
Liu et al., The effects of Chan Su extracts on the hematopoietic system of irradiated mice. *Chinese Journal of Hematology*, 7:405-407, 1986.
Zheng et al., Ex vivo expanded hematopoietic stem cells overcome the MHC barrier in allogeneic transplantation. *Cell Stem Cell*, 9:119-130, 2011.
Zheng et al., Inhibitory receptors bind Angptls and support blood stem cells and leukemia development. *Nature*, 485:656-660, 2012.
Gao et al., Comparison of toad venoms from different *Bufo* species by HPLC and LC-DAD-MS/MS. *J Ethnopharmacol*, 131:368-376, 2010.
Christensen and Weissman, Flk-2 is a marker in hematopoietic stem cell differentiation: a simple method to isolate long-term stem cells. *Proc Natl Acad Sci USA*, 98:14541-14546, 2001.
Cynshi et al., Effects of recombinant human erythropoietin on haemolytic anaemia in mice. *Br J Haematol*, 76:414-419. 1990.
Yamaguchi-Yamada et al., Improvement of anemia associated with chronic renal failure by recombinant human erythropoietin treatment in ICR-derived glomerulonephritis (ICGN) mice. *J Vet Med Sci*, 66:883-886, 2004.
Liu et al., "The effects of Chan Su extracts on multiple hematopoietic lineages of irradiated mice." Chinese Journal of Hematology, 7(7): 405-407, 1988.

What is claimed is:

1. A method of promoting regeneration of hematopoietic stem cells in a patient in need of regeneration of hematopoietic stem cells comprising administering to the patient a pharmaceutically effective amount of a compound in a substantially isolated or purified form and has the formula:

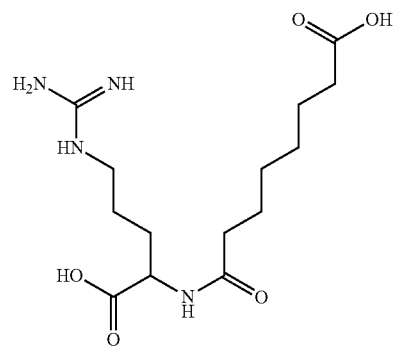 [SMILES: N=C(N)NCCCC(NC(=O)CCCCCCC(=O)O)C(=O)O]

wherein carbon 1 is in the R configuration, S configuration, or a mixture thereof; or a pharmaceutically acceptable salt or optical isomer thereof, wherein the compound is not comprised in a toad skin extract.

2. The method according to claim 1, wherein the regeneration of hematopoietic stem cells results in an increase in red blood cells.

3. The method according to claim 1, wherein the compound is administered with a surgery or second drug known to decrease the production of red blood cells.

4. The method of claim 3, wherein the compound is coadministered with the second drug selected from a chemotherapeutic agent, a radiotherapeutic agent, atovaquone, azacitidine, bexarotene, boceprevir, bosentan, bosutinib, brentuximab vedotin, carbidopa-levodopa, carglumic acid, decitabine, eribulin mesylate, foscarnet, metformin, ofatumumab, pomalidomide, prelatrexate solution, ropivacaine, rosiglitazone, sirolimus, temsirolimus, and valganciclovir.

5. The method of claim 3, wherein the compound mitigates or prevents the decrease in the production of red blood cells caused by the surgery or second drug.

6. The method according to claim 1, wherein the compound comprises 80% of the total mass of the substantially isolated or purified form.

7. The method of claim 1, wherein the compound comprises 90% of the total mass of the substantially isolated or purified form.

8. The method of claim 1, wherein carbon 1 is in the R configuration.

9. The method of claim 1, wherein carbon 1 is in the S configuration.

10. The method of claim 1, wherein carbon 1 comprises a mixture of formulas in the R and S configuration.

* * * * *